(12) United States Patent
Moskowitz et al.

(10) Patent No.: US 7,083,650 B2
(45) Date of Patent: Aug. 1, 2006

(54) ARTIFICIAL EXPANSILE TOTAL LUMBAR AND THORACIC DISCS FOR POSTERIOR PLACEMENT WITHOUT SUPPLEMENTAL INSTRUMENTATION AND ITS ADAPTATION FOR ANTERIOR PLACEMENT OF ARTIFICIAL CERVICAL, THORACIC AND LUMBAR DISCS

(76) Inventors: Nathan C. Moskowitz, 212 North Adams St., Rockville, MD (US) 20850; Mosheh Moskowitz, 212 North Adams St., Rockville, MD (US) 20850

( * ) Notice: Subject to any disclaimer, the term of this patent is extended or adjusted under 35 U.S.C. 154(b) by 33 days.

(21) Appl. No.: 11/019,351

(22) Filed: Dec. 23, 2004

(65) Prior Publication Data

US 2005/0261769 A1    Nov. 24, 2005

Related U.S. Application Data

(63) Continuation-in-part of application No. 10/964,633, filed on Oct. 15, 2004.

(60) Provisional application No. 60/578,319, filed on Jun. 10, 2004, provisional application No. 60/573,346, filed on May 24, 2004, provisional application No. 60/572,468, filed on May 20, 2004, provisional application No. 60/570,837, filed on May 14, 2004, provisional application No. 60/570,098, filed on May 12, 2004.

(51) Int. Cl.
*A61F 2/44* (2006.01)

(52) U.S. Cl. ...................... 623/17.11; 606/61
(58) Field of Classification Search .. 623/17.11–17.16; 606/61, 78
See application file for complete search history.

(56) References Cited

U.S. PATENT DOCUMENTS

| | | | |
|---|---|---|---|
| 5,123,926 A | 6/1992 | Pisharodi | |
| 5,514,180 A | 5/1996 | Heggeness et al. | |
| 5,782,832 A * | 7/1998 | Larsen et al. | 606/61 |
| 6,126,689 A * | 10/2000 | Brett | 623/17.16 |
| 6,368,350 B1 | 4/2002 | Erickson et al. | |
| 6,375,682 B1 * | 4/2002 | Fleischmann et al. | 623/17.12 |
| 6,419,704 B1 | 7/2002 | Ferree | |
| 6,458,159 B1 | 10/2002 | Thalgott | |
| 6,527,804 B1 | 3/2003 | Gauchet et al. | |
| 6,533,818 B1 | 3/2003 | Weber et al. | |
| 6,572,653 B1 * | 6/2003 | Simonson | 623/17.13 |

(Continued)

OTHER PUBLICATIONS

Traynelis, Vincent C., M.D., "Prosthetics and Biologics: The Wave of the Future," Clinical Neurosurgery, vol. 50, Proceedings of the Congress of Neurological Surgeons, Philadelphia, PA 2002, Chapter 9, pp. 207-219.

(Continued)

*Primary Examiner*—Eduardo C. Robert
*Assistant Examiner*—Richard Shaffer
(74) *Attorney, Agent, or Firm*—McGrath, Geissler, Olds & Richardson, PLLC

(57) ABSTRACT

A total artificial expansible disc having at least two pairs of substantially parallel shells, which move in multiple directions defined by at least two axes, is disclosed. Several methods for implanting the total artificial expansile disc are also disclosed. The total artificial expansile disc occupies a space defined by a pair of vertebral endplates. An expansion device, which preferably includes a jackscrew mechanism, moves the pairs of shells in multiple directions. A core is disposed between the pairs of shells, and the core permits the vertebral endplates to move relative to one another.

68 Claims, 35 Drawing Sheets

U.S. PATENT DOCUMENTS

| | | |
|---|---|---|
| 6,579,318 B1 | 6/2003 | Varga et al. |
| 6,582,468 B1 | 6/2003 | Gauchet |
| 6,641,614 B1 * | 11/2003 | Wagner et al. ............ 623/17.15 |
| 6,719,794 B1 | 4/2004 | Gerber |
| 6,723,126 B1 * | 4/2004 | Berry ....................... 623/17.11 |
| 6,733,532 B1 | 5/2004 | Gauchet et al. |
| 6,764,491 B1 | 7/2004 | Frey et al. |
| 6,770,094 B1 | 8/2004 | Fehling et al. |
| 2004/0088054 A1 * | 5/2004 | Berry ....................... 623/17.11 |

OTHER PUBLICATIONS

Wai, E.K. et al., Disk Replacement Arthroplasties: Can The Success of Hip and Knee Replacements be Repeated in the Spine?, Seminars in Spine Surgery, vol. 15, No. 4 (Dec.) 2003: pp. 473-482.

Guyer, Richard D. et al., "Intervertebral Disc Prostheses," SPINE Journal, vol. 28, No. 15S, Supp. To Aug. 1, 2003, pp. S15-S23.

* cited by examiner

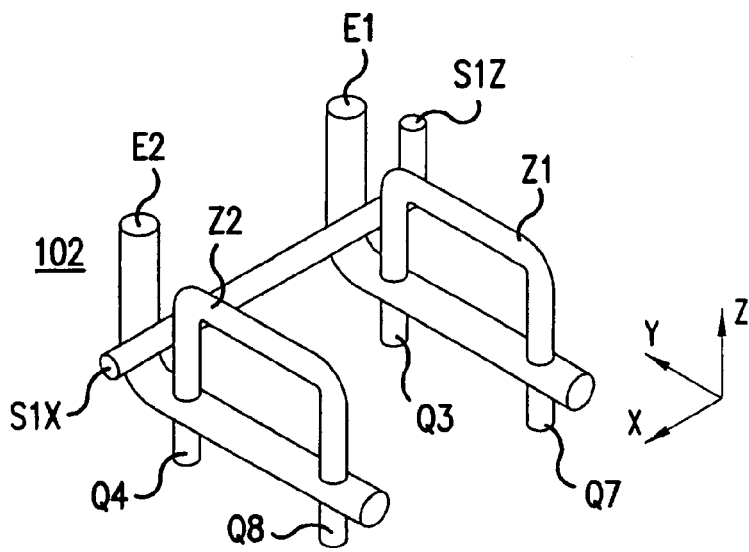
FIG.4K(1)
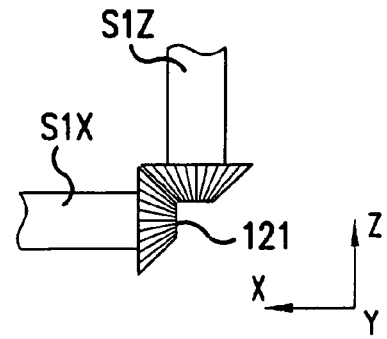
FIG.4K(2)
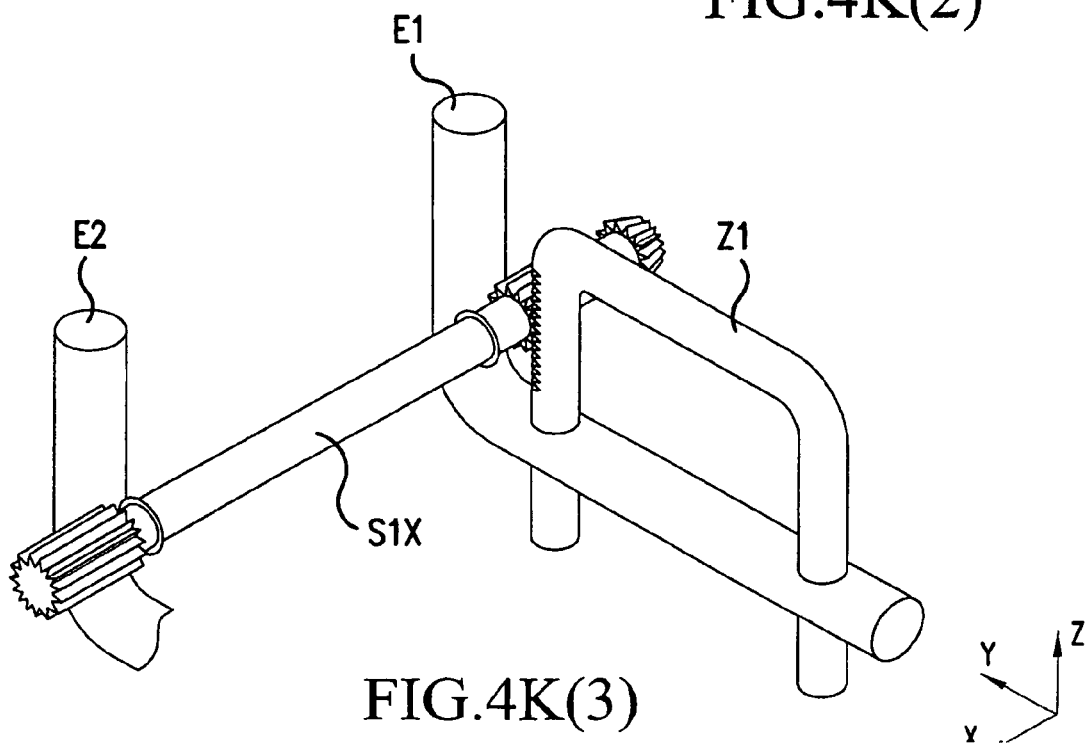
FIG.4K(3)

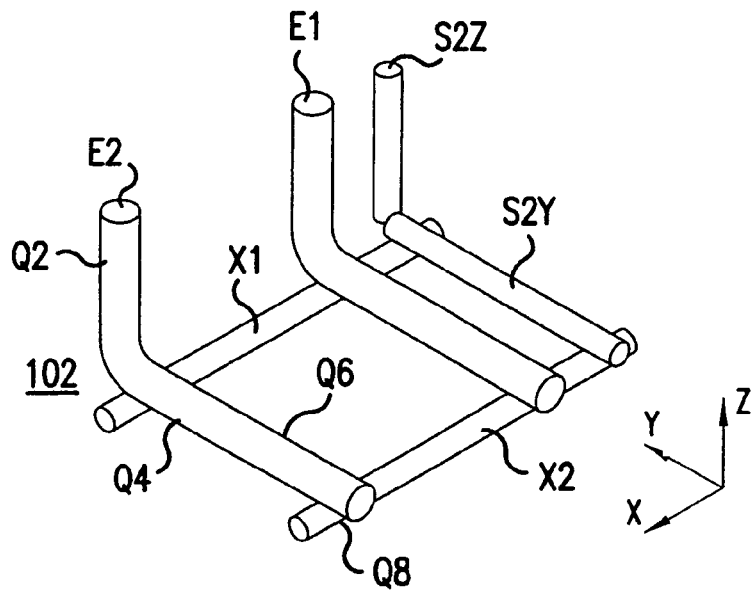
FIG.4L(1)
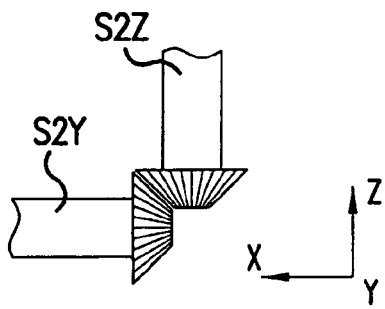
FIG.4L(2)
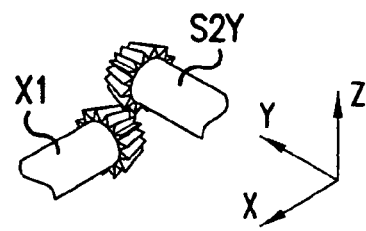
FIG.4L(3)
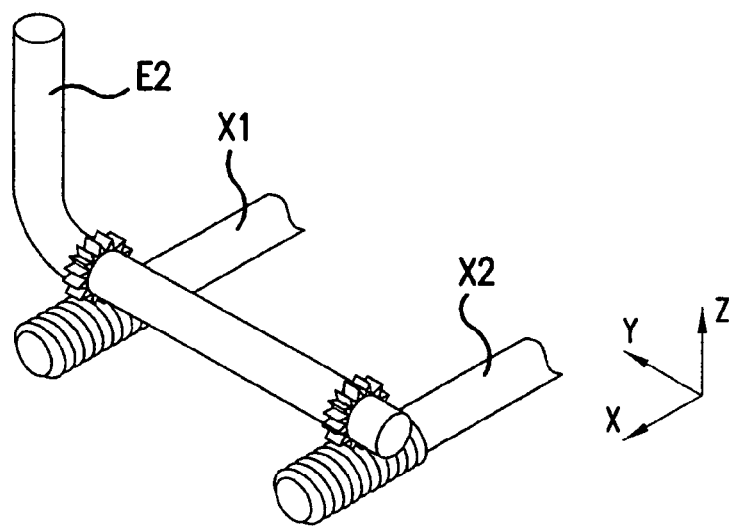
FIG.4L(4)

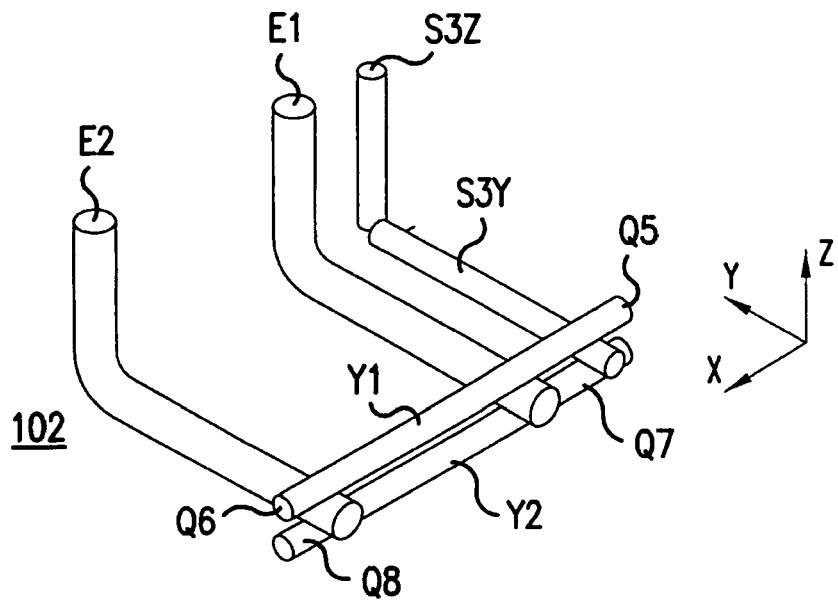
FIG.4M(1)
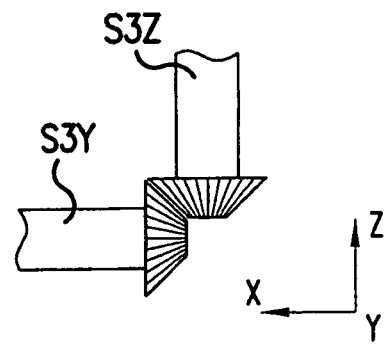
FIG.4M(2)
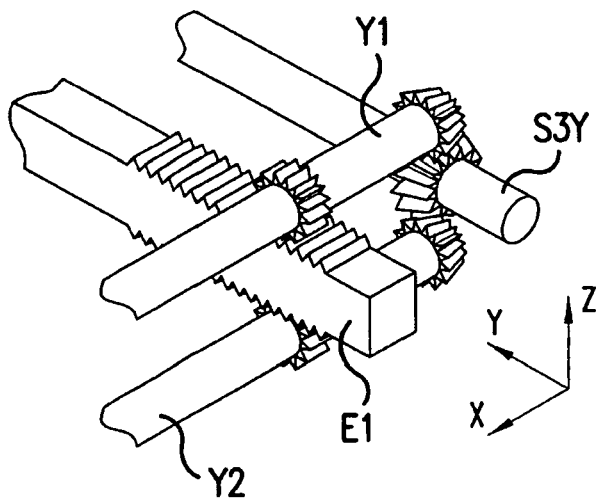
FIG.4M(3)

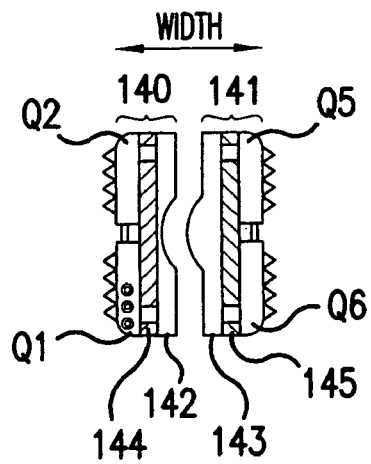
FIG.6A(1)
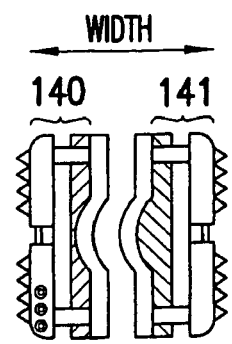
FIG.6A(2)
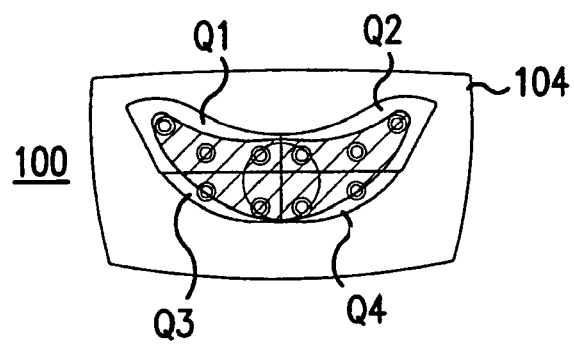
FIG.6B(1)
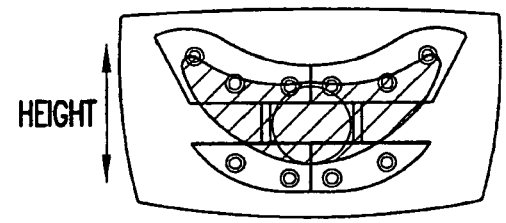
FIG.6B(2)
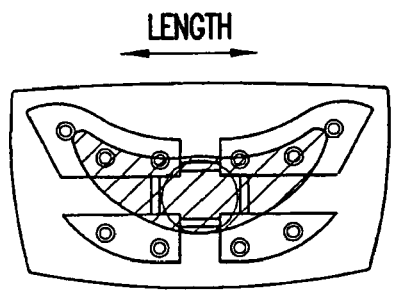
FIG.6B(3)

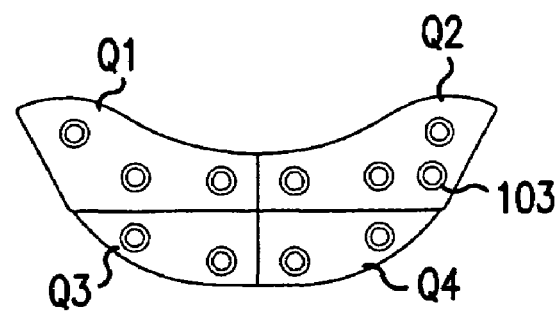
FIG.6C(1)
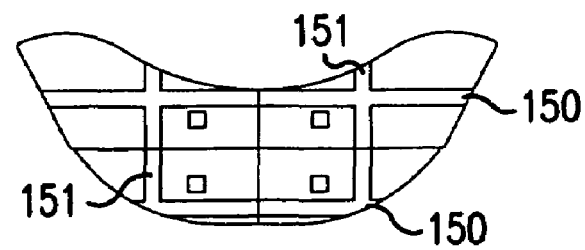
FIG.6C(2)
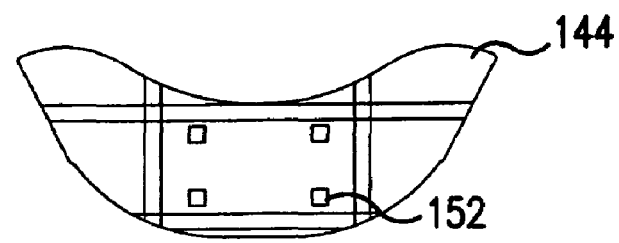
FIG.6C(3)
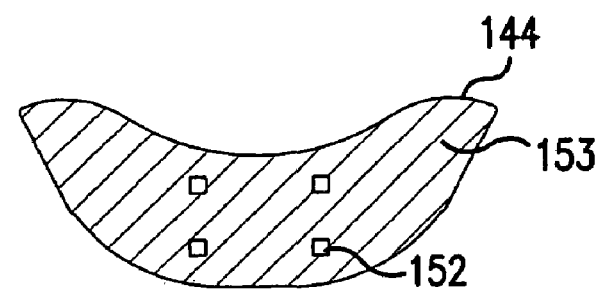
FIG.6C(4)

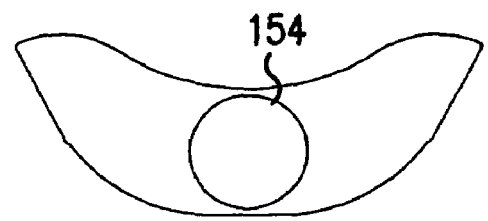
FIG.6C(5)
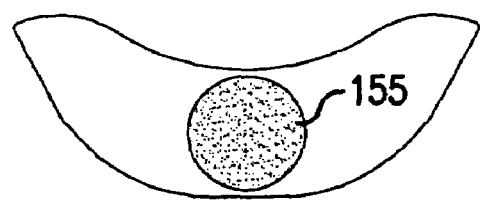
FIG.6C(6)
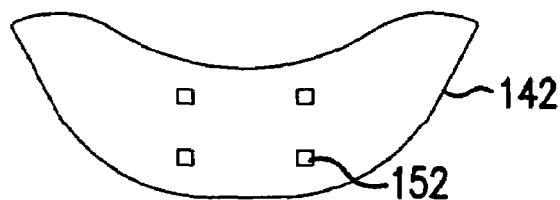
FIG.6C(7)
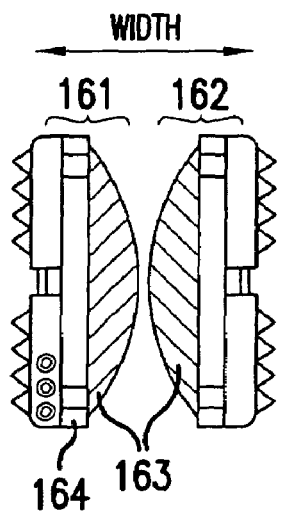
FIG.7A(1)
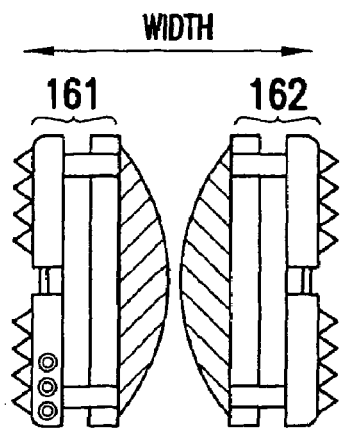
FIG.7A(2)

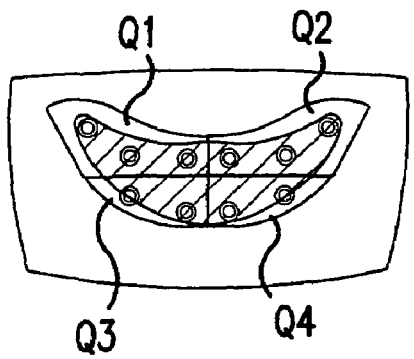
FIG.7B(1)
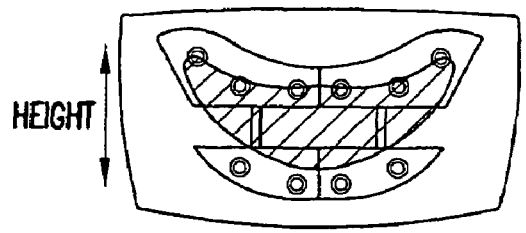
FIG.7B(2)
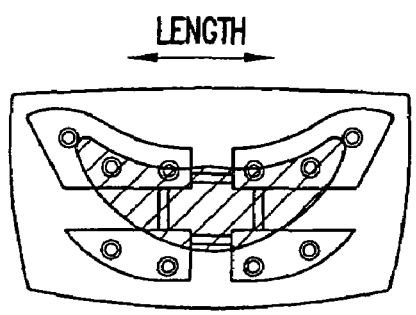
FIG.7B(3)
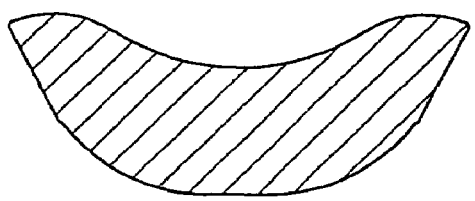
FIG.7C(1)
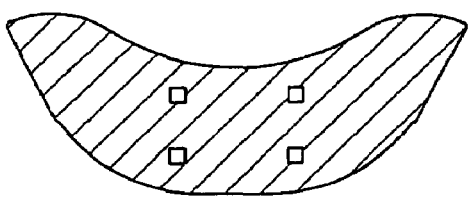
FIG.7C(2)

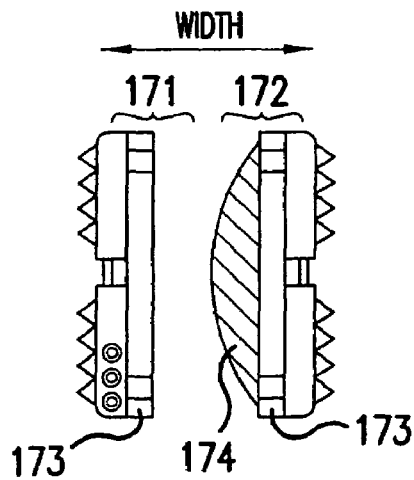
FIG.8A
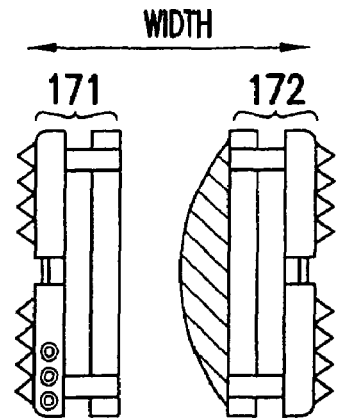
FIG.8B
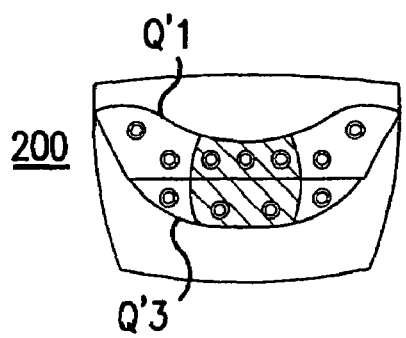
FIG.9A(1)
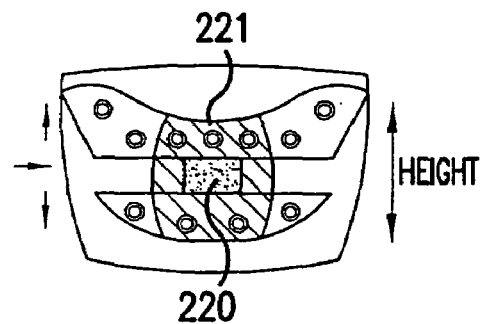
FIG.9A(2)
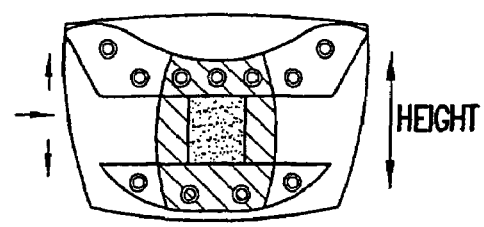
FIG.9A(3)

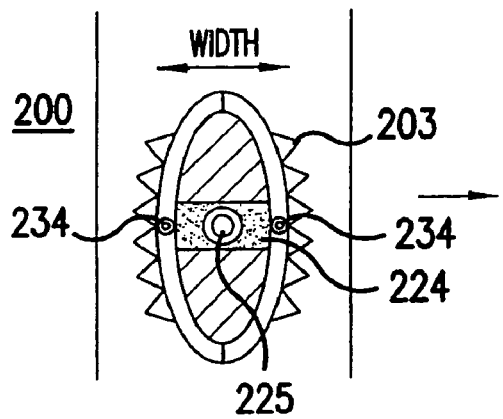
FIG.9B(1)
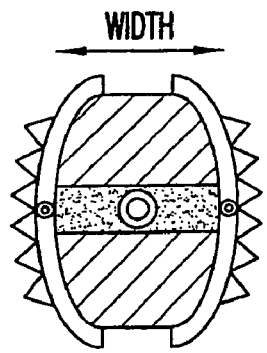
FIG.9B(2)
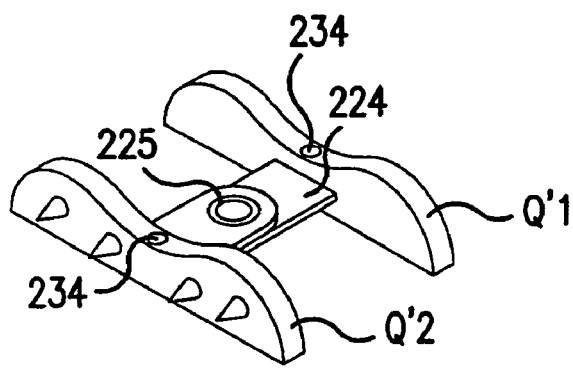
FIG.9C(1)
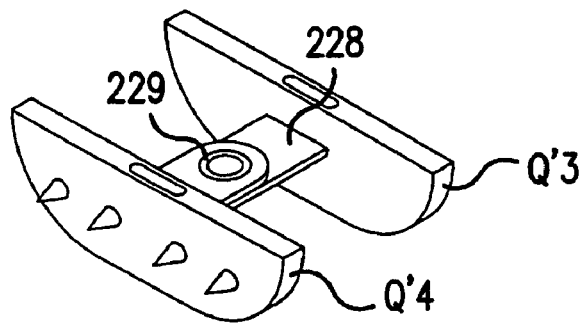
FIG.9C(2)

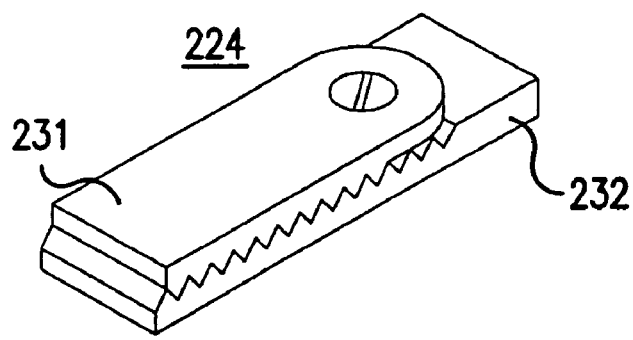
FIG.9D(1)
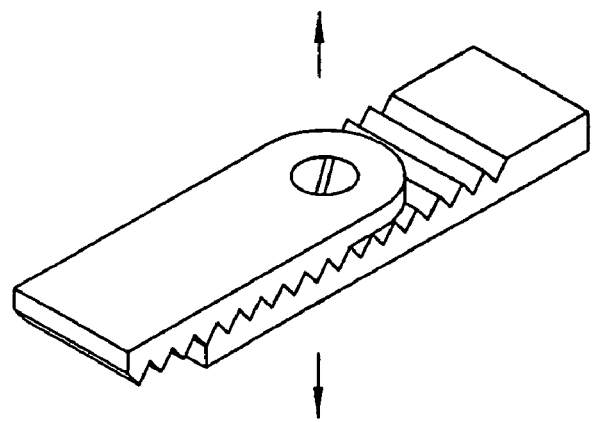
FIG.9D(2)
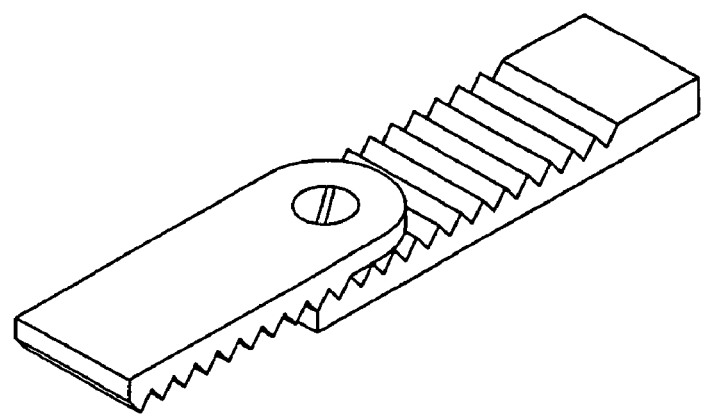
FIG.9D(3)

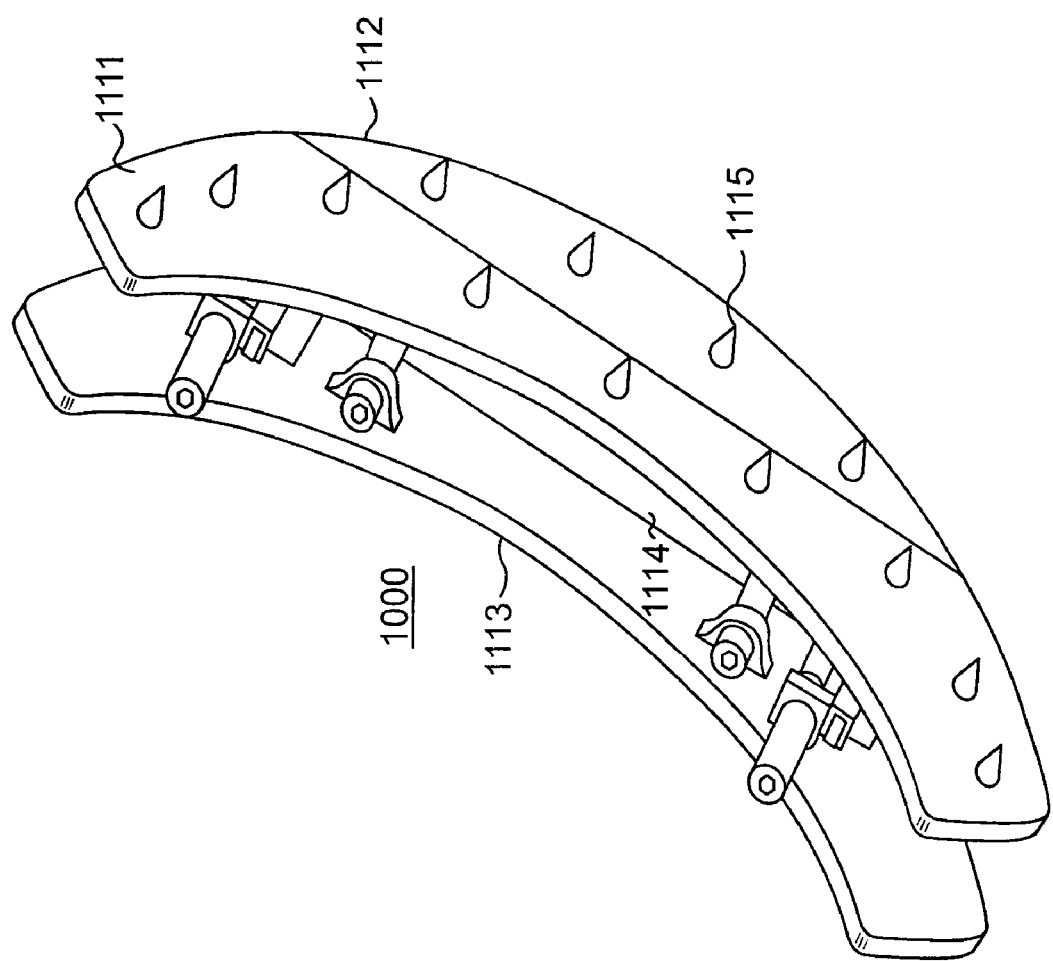
FIG. 10A1

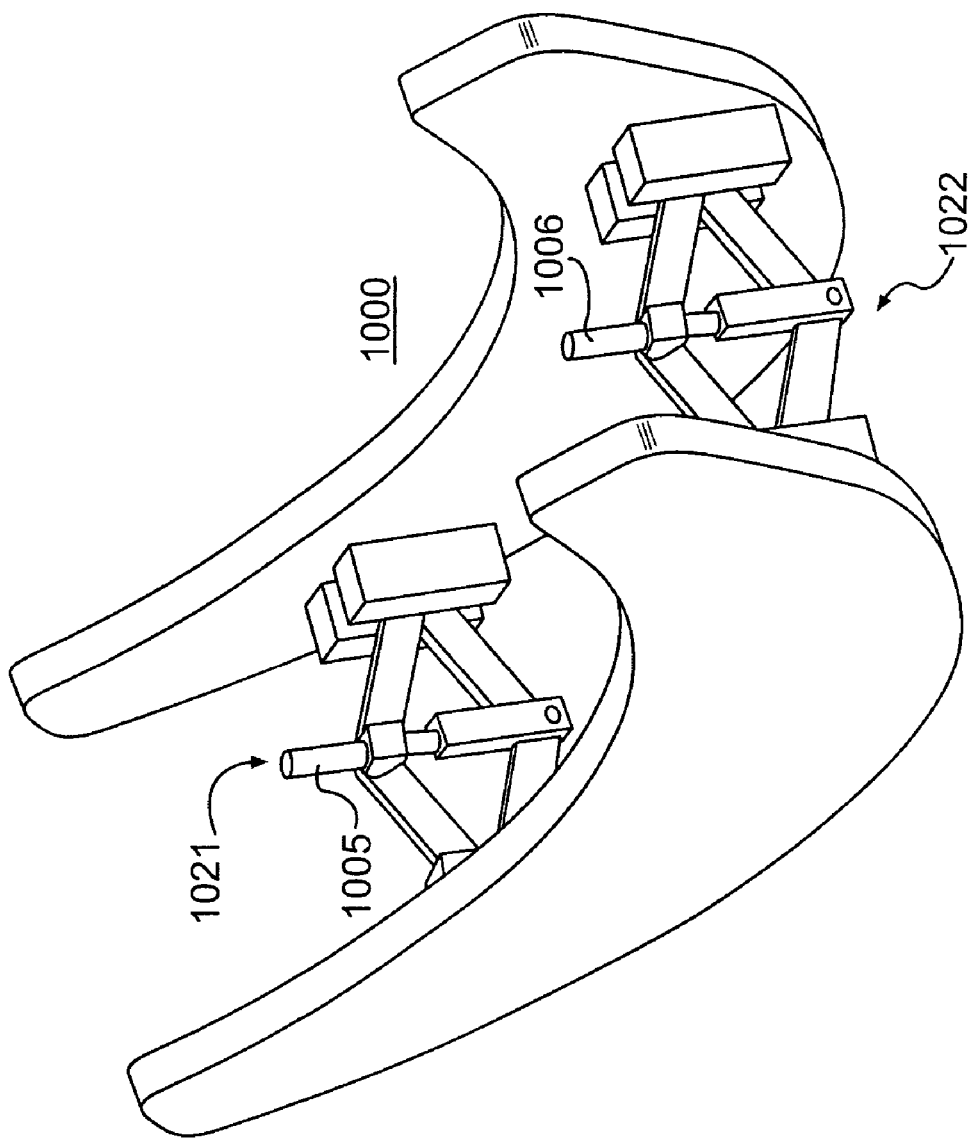
FIG. 10A2

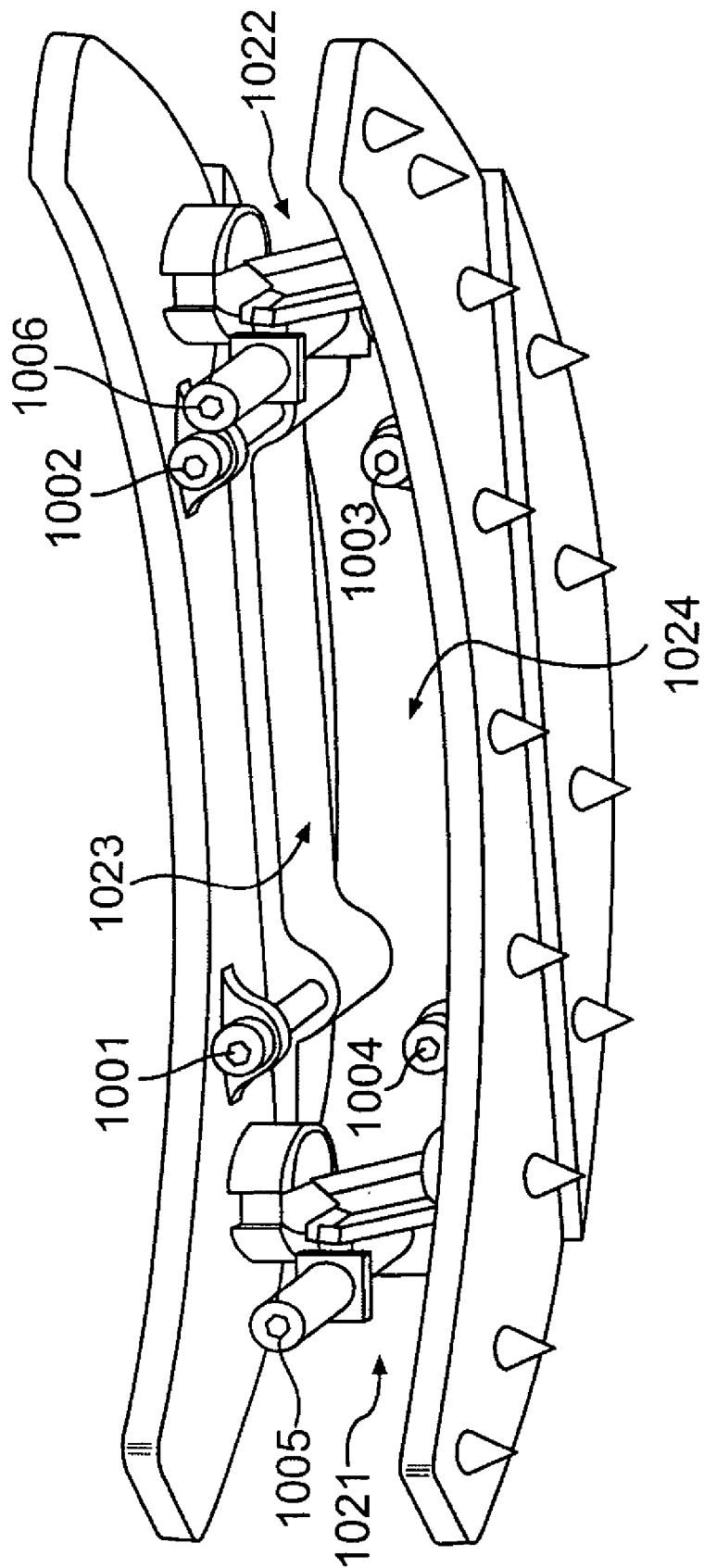
FIG. 10A3

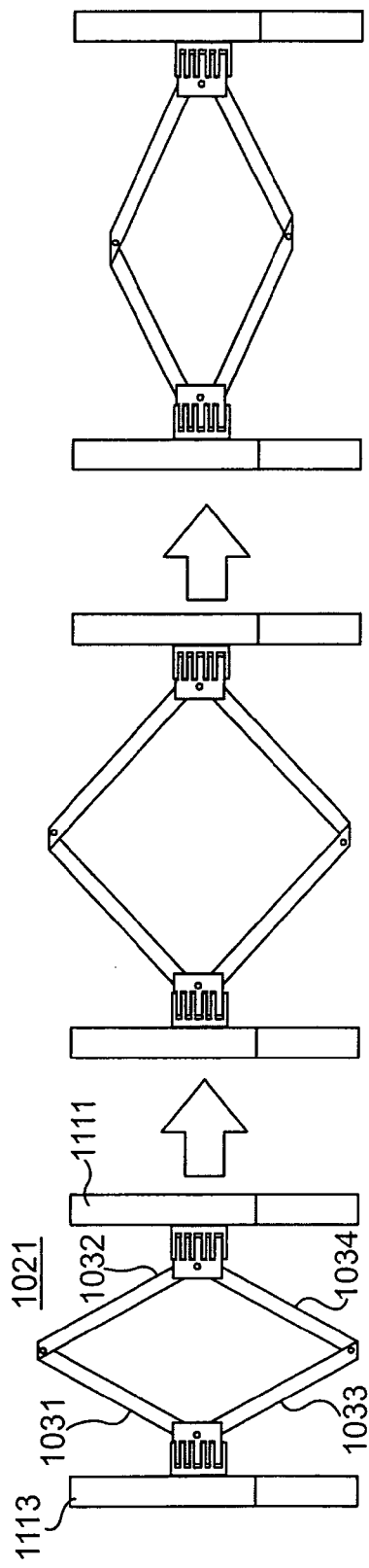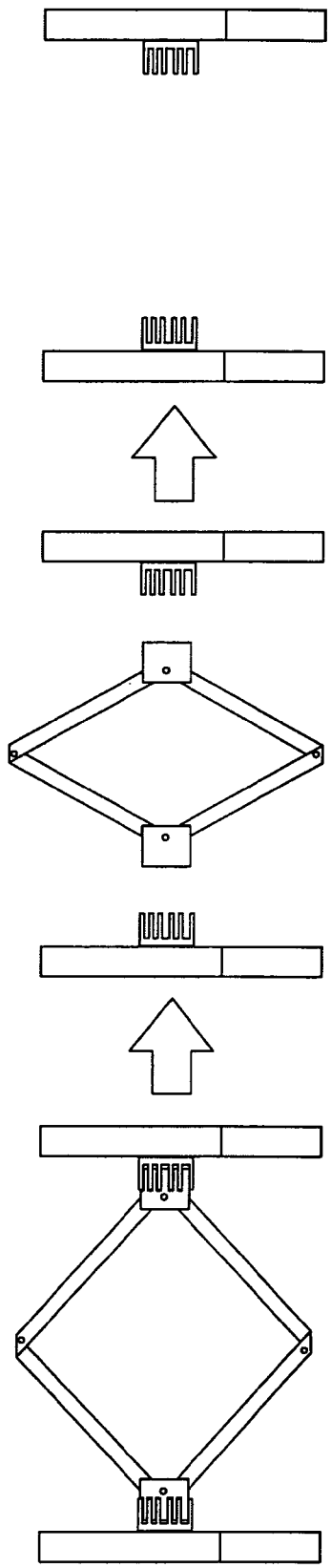
FIG. 11A1  FIG. 11A2  FIG. 11A3  FIG. 11A4  FIG. 11A5  FIG. 11A6

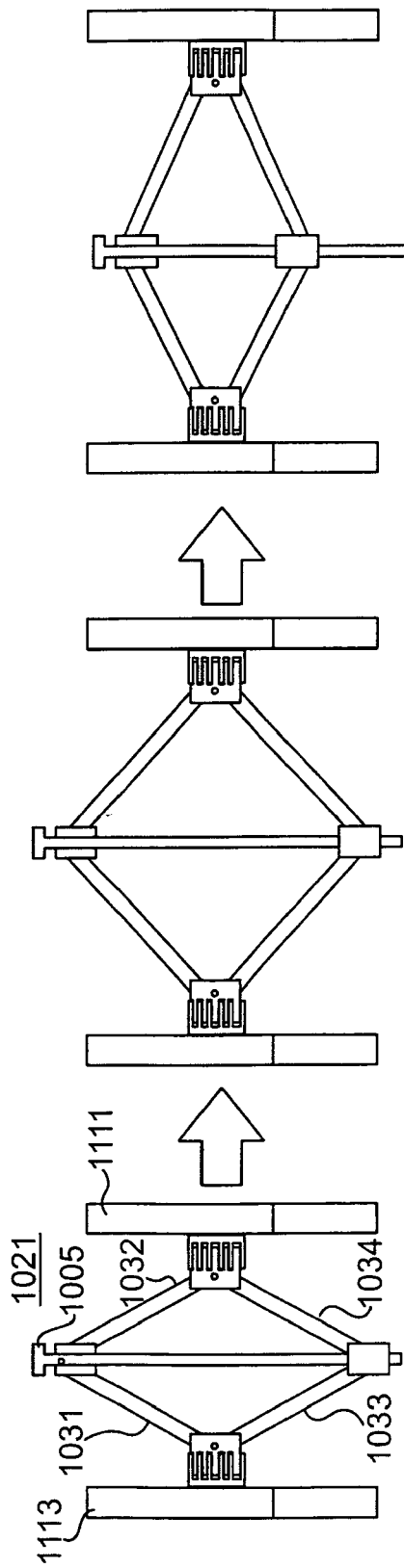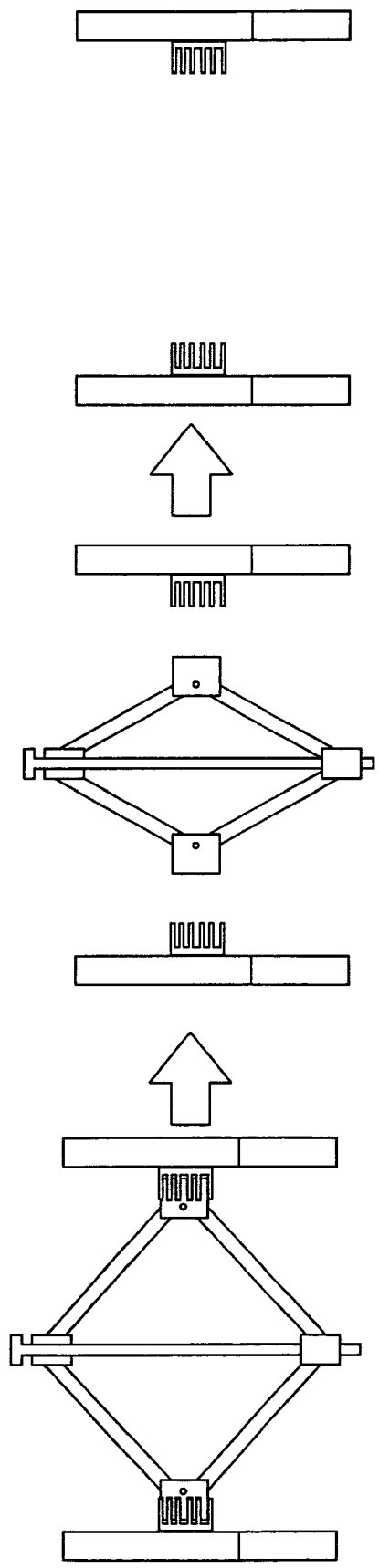

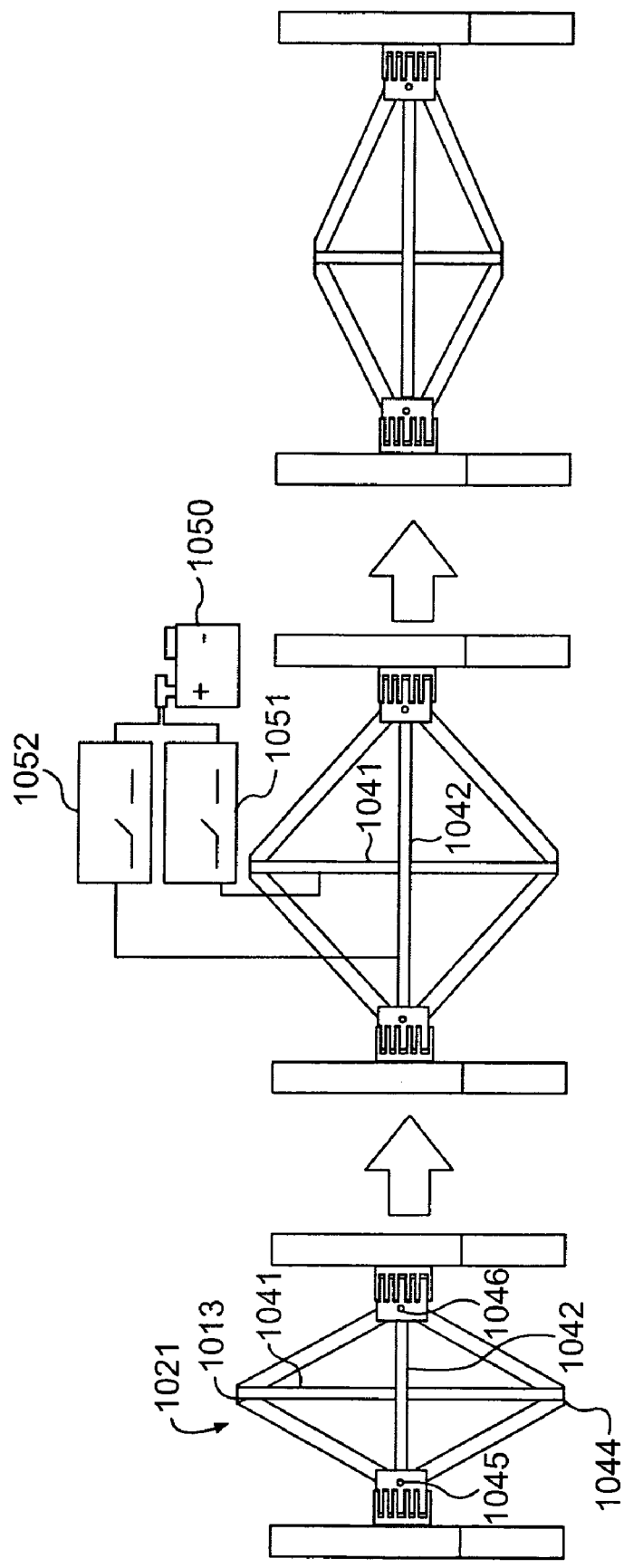

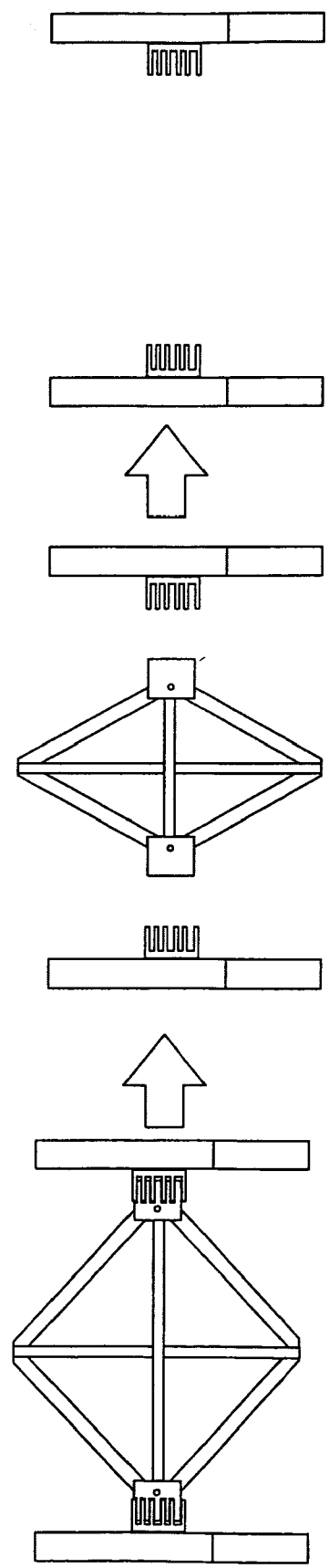

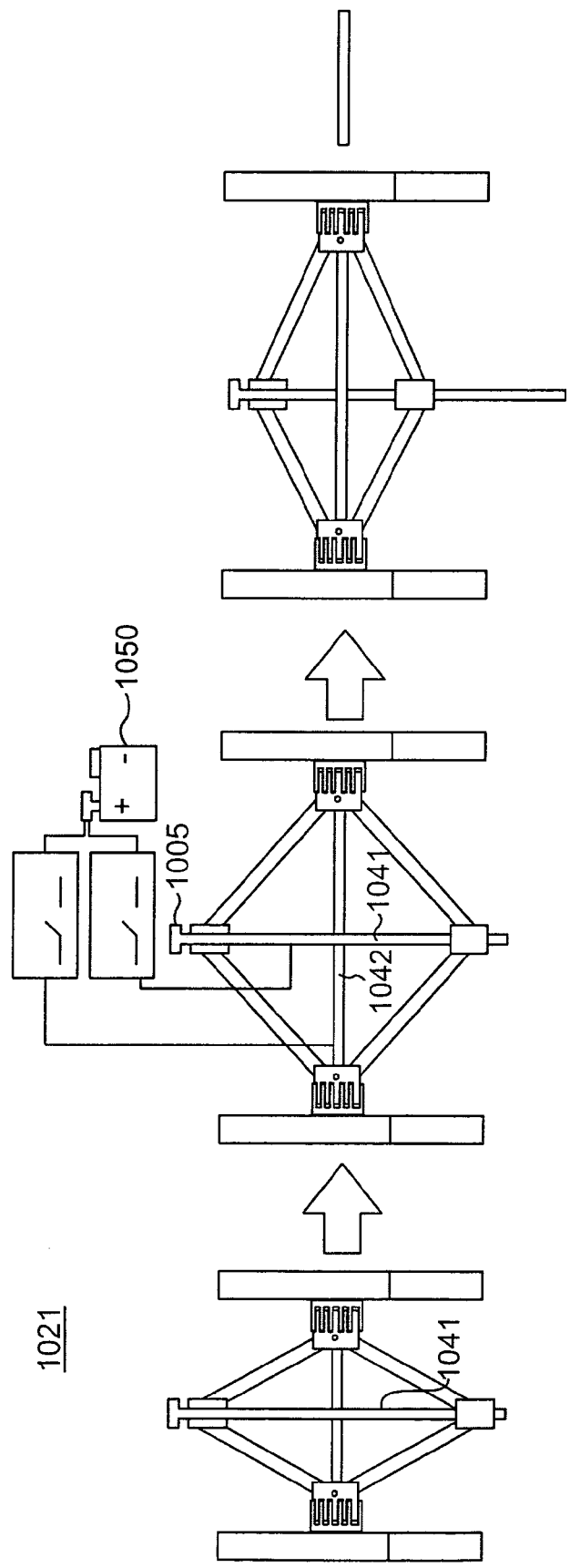
FIG. 11D3
FIG. 11D2
FIG. 11D1

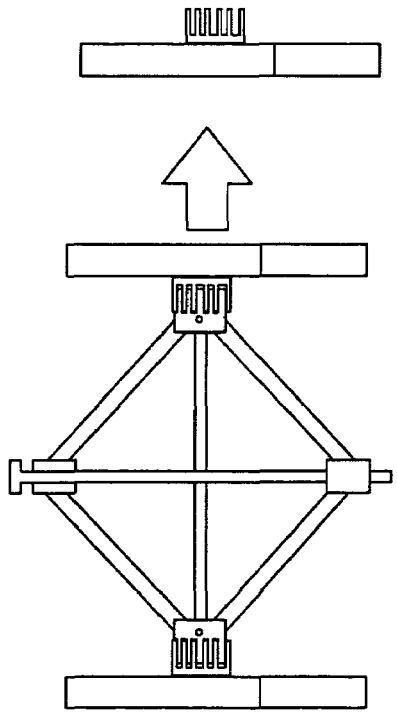
FIG. 11D4
FIG. 11D5
FIG. 11D6

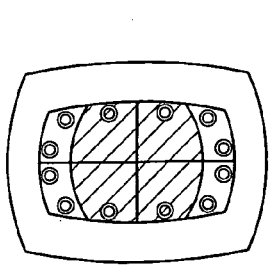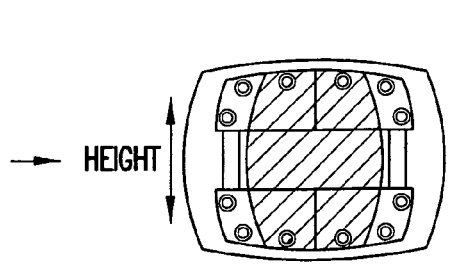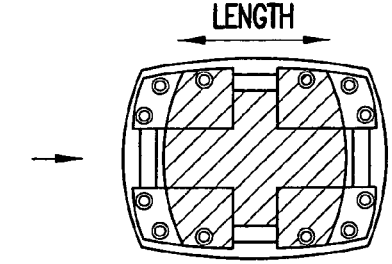
FIG.13A(1)    FIG.13A(2)    FIG.13A(3)
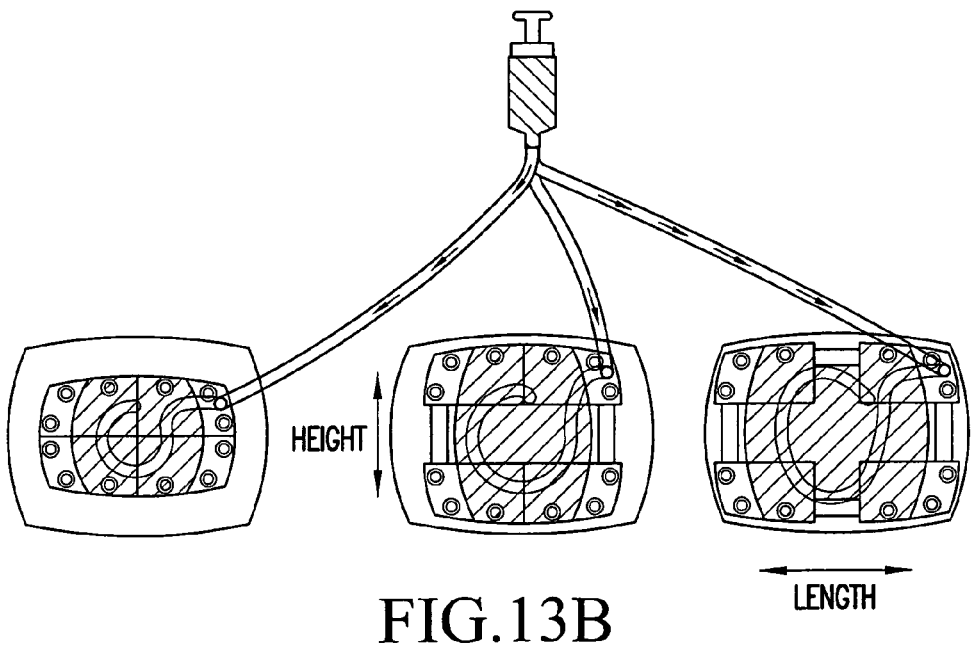
FIG.13B

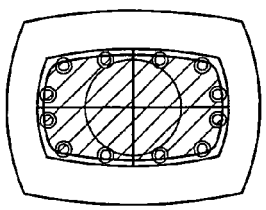 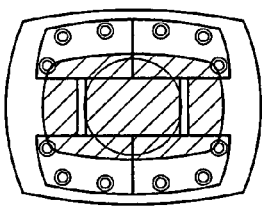 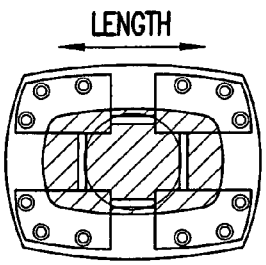
FIG.13C(1)   FIG.13C(2)   FIG.13C(3)
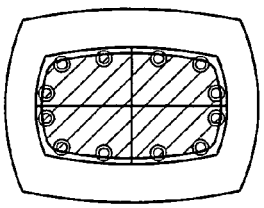 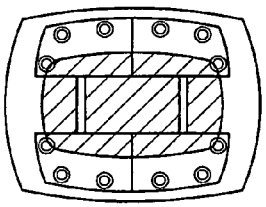 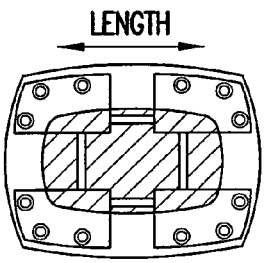
FIG.13D(1)   FIG.13D(2)   FIG.13D(3)

ARTIFICIAL EXPANSILE TOTAL LUMBAR AND THORACIC DISCS FOR POSTERIOR PLACEMENT WITHOUT SUPPLEMENTAL INSTRUMENTATION AND ITS ADAPTATION FOR ANTERIOR PLACEMENT OF ARTIFICIAL CERVICAL, THORACIC AND LUMBAR DISCS

This application is continuation-In-Part of copending application Ser. No. 10/964,633, filed on Oct. 15, 2004, which claims the benefit under Title 35, U.S.C. §119 (e) of U.S. provisional application 60/578,319 filed on Jun. 10, 2004; 60/573,346 filed on May 24, 2004; 60/572,468 filed on May 20, 2004; 60/570,837 filed on May 14, 2004; and 60/570,098 filed on May 12, 2004, the entire contents of which are hereby incorporated by reference and for which priority is claimed under 35 U.S.C. § 120.

BACKGROUND OF THE INVENTION

1. Field of the Invention

The present invention relates to artificial discs, and more specifically relates to artificial expansile total lumbar and thoracic discs for posterior placement without supplemental instrumentation, and to anterior placement of artificial discs for the cervical, thoracic and lumbar spine.

2. Description of the Relevant Art

Cervical and lumbar total artificial discs are entering the clinical neurosurgical and orthopedic markets. The benefits of these artificial discs are well known. They replace diseased discs, and preserve motion segment mobility. Discogenic and radicular pain are relieved without forfeiting segmental mobility, which is typical of traditional anterior or posterior lumbar fusions. Total artificial disc replacements aim to cover the entire expanse of the disc space because restoration of range of motion is reportedly greatest when roughly 80% of the vertebral endplate is covered. Thus it is only rational, currently to place prosthetic discs anteriorly where access can be easily obtained, and they can be secured by a variety of anterior screw fixations. This technology is adequate for single level disc replacement in the cervical spine. However based on the current anterior cervical prosthetic disc screw fixation methodology its implantation is periodically complicated by screw failures e.g. partial or complete screw pullouts or breaks, and in most designs it is limited to single level replacement. Furthermore, for lumbar total artificial discs, placement is limited to only the L4/5 and L5/S1 disc spaces, and not above, secondary to aortic and vena caval anatomical restraints. Likewise, for the thoracic spine. Thus far no type of thoracic prosthetic disc device has been reported or described. Furthermore, despite the purported safety of placement of the current total lumbar artificial discs, there is a significant risk of retrograde ejaculations in males, and the risk of vascular injury, which although small, is potentially catastrophic if it occurs.

The design of total artificial discs, which began in the 1970's, and in earnest in the 1980's, consists essentially of a core (synthetic nucleus pulposus) surrounded by a container (pseudo-annulus). Cores have consisted of rubber (polyolefin), polyurethane (Bryan-Cervical), silicon, stainless steel, metal on metal, ball on trough design (Bristol-Cervical, Prestige-Cervical), Ultra High Molecular Weight Polyethylene (UHMWPE) with either a biconvex design allowing unconstrained kinematic motion (Link SB Charite-Lumbar), or a monoconvex design allowing semiconstrained motion (Prodisc-Lumbar). There is also a biologic 3-D fabric artificial disc interwoven with high molecular weight polyethylene fiber, which has only been tested in animals. Cervical and lumbar artificial discs are premised on either mechanical or viscoelastic design principles. The advantages of mechanical metal on metal designs including the stainless steel ball on trough design and the UHMWPE prostheses include their low friction, and excellent wear characteristics allowing long term motion preservation. Their major limitation is the lack of elasticity and shock absorption capacity. The favorable features of the viscoelastic prosthetics include unconstrained kinematic motion with flexion, extension, lateral bending, axial rotation and translation, as well as its cushioning and shock absorption capacity. On the other hand, their long term durability beyond ten years is not currently known. Containers have consisted of titanium plates, cobalt chrome or bioactive materials. This history is reviewed and well documented in Guyer, R. D., and Ohnmeiss, D. D. "Intervertebral disc prostheses", Spine 28, Number 15S, S15-S23, 2003; and Wai, E. K., Selmon, G. P. K. and Fraser, R. D. "Disc replacement arthroplasties: Can the success of hip and knee replacements be repeated in the spine?", Seminars in Spine Surgery 15, No 4: 473–482, 2003.

It would be ideal if total lumbar artificial discs could be placed posteriorly allowing access to all levels of the lumbar spine. Also one could place these devices posteriorly in thoracic disc spaces through a transpedicular approach. Similarly if these devices can be placed anteriorly particularly in the cervical spine without anterior screw fixation, and custom-fit it for each disc in each individual, the ease of placement would reduce morbidity and allow for multi-level disc replacement. Placement of an artificial disc in the lumbar spine if inserted posteriorly through a unilateral laminotomy by using a classical open microscopic approach or by using a minimally invasive tubular endoscopic approach would significantly reduce the possibility of recurrent disc herniation. If placed without facet joint violation, or with only unilateral mesial facetectomy, and the device can purchase the endplates with spikes there would be no need for supplemental posterior pedicle screw fixation, thus obviating the associated morbidity associated with pedicle screws and bone harvesting. To take it one step further, if artificial lumbar discs can be posteriorly placed successfully and safely throughout the entire lumbar spine, every routine lumbar discectomy could be augmented by artificial disc placement which would simultaneously eliminate discogenic and radicular pain while preserving flexibility. Furthermore by so doing, the probability of recurrent herniation plummets, and subsequently the need for posterior pedicle instrumentation plummets, thereby diminishing overall spinal morbidity, expenditure, and leading to the overall improvement in the quality of life.

Presumably up to now, technology is not focusing on posterior placement of total lumbar prosthetic discs because of inadequate access to the disc space posteriorly. To circumvent this problem others have been working on the posterior placement, not of a total prosthetic disc but of a prosthetic disc nucleus (PDN), or essentially a core without a container (pseudo annulus). PDNs, which are considered post-discectomy augmentations, have consisted of one of the following materials: 1) hydrogel core surrounded by a polyethylene jacket (Prosthetic Disc Nucleus). Two of these devices have to be put in. There is a very high, 38% extrusion rate, 2) Polyvinyl alcohol (Aquarelle), 3) polycarbonate urethane elastomer with a memory coiling spiral (Newcleus), 4) Hydrogel memory coiling material that hydrates to fill then disc space, 5) Biodisc consisting of in-situ injectable and rapidly curable protein hydrogel, 6)

Prosthetic Intervertebral Nucleus (PIN) consisting of a polyurethane balloon implant with in-situ injectable rapidly curable polyurethane and 7) thermopolymer nucleus implant. (See the two publications identified above). The approach of posteriorly placing artificial disc cores appears to be flawed in that: 1) there is a high extrusion rate, 2) it lacks good fixation as does total prosthetic devices that are placed anteriorly, 3) it is restricted only to early symptomatically disrupted discs which have only nucleus pulposus but not annulus or endplate pathology, and 4) are contraindicated in discs with an interspace height of less than 5 mm.

DESCRIPTION OF THE DRAWINGS

FIGS. 4A–M illustrate in detail the mechanical cylinder-spur-gear-spring (CSGS) system incorporated into the cross-connecting 8 titanium shells of the three-dimensional Lumbar/Thoracic prosthesis which enable expansion of the device in x, y and z dimensions. A system of springs is incorporated into the y-axis of the CSGS so as not to hinder the flexibility of the inner core.

FIGS. 6A, 6B and 6C illustrate a third embodiment of the expansile total lumbar/thoracic artificial disc implant, i.e., this illustrates a mechanical metal on metal, stainless steel, ball on trough design (Embodiment III);

FIGS. 7A, 7B and 7C illustrate a fourth embodiment of the three-dimensional expansile total lumbar/thoracic artificial disc implant, i.e., this illustrates a mechanical metal on metal, biconvex ultra high molecular weight polyethylene (UHMWPE) design (Embodiment IV);

FIG. 8 illustrates a fifth embodiment of the three-dimensional expansile total lumbar/thoracic artificial disc implant, i.e., this illustrates a mechanical metal on metal, monoconvex UHMWPE design (Embodiment V);

FIGS. 9A–E illustrate a sixth embodiment of the expansile total lumbar/thoracic artificial disc implant. This simpler design expands in two not three dimensions (height and width). The mechanism of expansion is based on calibrated ratcheting of corrugated interconnected bars. FIGS. 9A–E therefore represent a two-dimensional expansile prosthesis, using the elastic polymer nuclear design as the prototype (Embodiment VI);

FIGS. 10A–E illustrate a seventh embodiment of the expansile total lumbar/thoracic artificial disc implant which expands in two dimensions using a jackscrew width expansion mechanism and a fixed-screw height expansion mechanism (Embodiment VII).

FIGS. 11A–D illustrate the precise mechanism of the jackscrew opening and closing employed in embodiment VII. The figures illustrate four types of mechanisms; mechanical using a screw, electrical-wired control, electrical-wireless control, and a hybrid mechanical-electrical mechanism combining a screw and wired control.

FIGS. 13A, 13B, 13C and 13D illustrate a cross-section of the prostheses adapted for anterior implantation into the cervical disk space. FIG. 13A illustrates the expandable elastic polymer nucleus design (Embodiment I). FIG. 13B illustrates the in-situ injection/expansion elastic polymer nucleus design (Embodiment II). FIG. 13C illustrates the mechanical, metal on metal, stainless steel, ball on trough design (Embodiment II). FIG. 13D illustrates the mechanical, metal on metal, UHMWPE biconvex or monoconvex design (Embodiments IV and V).

DESCRIPTION OF THE PREFERRED EMBODIMENTS

The Medical Device

Referring now to FIGS. 1–4, the above described problem can be solved in the lumbar/thoracic spine by the insertion of a total boomerang (bean) shaped prosthetic disc 100 including an expansile disc core 101 surrounded by ratchetable titanium shells (containers) Q1–Q8 that can expand geometrically in all three x, y, and z planes, horizontally, vertically and width wise.

The outer titanium shells Q1–Q8 themselves when ratcheted width-wise have titanium spikes 103 inserting themselves into and purchasing the endplates, thus securing permanent integration into the vertebral endplates. The outer shell titanium surfaces can be treated with hydroxyappetite to facilitate bone incorporation. There is currently available a vertebral ratcheting corpectomy construct which can be ratcheted up vertically until it purchases the rostral and caudal endplates with spikes. There are currently transpedicular/posterior lumbar interbody fusion (T/PLIF) bean shaped constructs, which can be unilaterally inserted into disc spaces. There are currently static total artificial discs (anteriorly placed). The present invention, however, constructs an expansile disc core within a boomerang (bean) shaped titanium construct which can be unilaterally inserted posteriorly into the lumbar and thoracic disc spaces, and can then be ratcheted in vertical and horizontal dimensions to custom fit the implant with the height and length of the individual vertebral body, and ratcheted width wise to conform to the individual width of the a disc space. This total prosthetic device can be secured to the endplates with spike attachments (teeth).

Figure 1A:
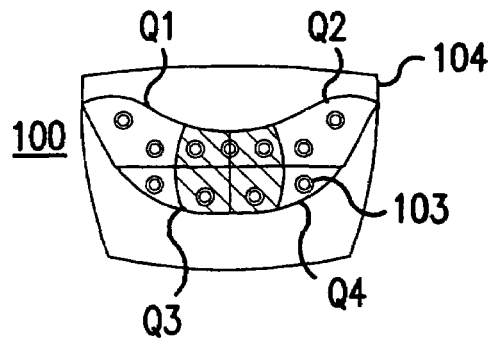
FIG. 1 illustrates a cross-section of the, expansile total lumbar/thoracic implant upon initial posterior insertion into the lumbar (or thoracic) disc space against the background of a vertebral body, i.e., this illustrates a three-dimensional expandable elastic polymer nucleus design (Embodiment I)
Figure 1B:
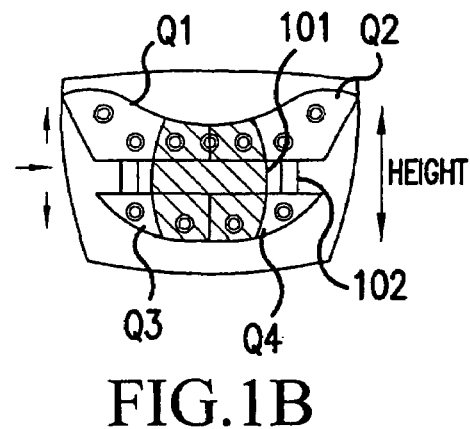
Figure 1C:
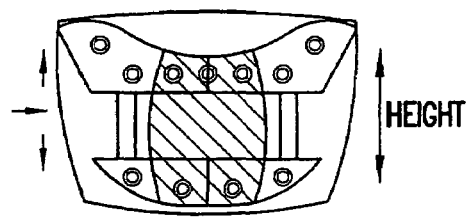

FIG. 1 illustrates a cross-section of the implant 100 upon initial posterior insertion into the lumbar (or thoracic) disc space 104 against the background of a vertebral body. Note the expansile elastic polymer nucleus 101, surrounded by an elastometric sheath, which is molded to (vulcanized) the inner surface of the outer titanium shells. Note the titanium spikes 103. In FIG. 1A, it should be noted that the spikes are on four separate titanium plates (shells) Q1–Q4 which currently are adjacent to each other. This represents one of two leaflets of the device (rostral and caudal). Hence there are a total of eight moveable titanium shells Q1–Q8. Upon ratcheting the height up with a screwdriver, the device 100 can be fine-tuned to the individual vertebral body height (FIG. 1). In FIG. 1B, an expansion device 102 causes the shells Q1, Q2 to separate from shells Q3, Q4.

Figure 2A:
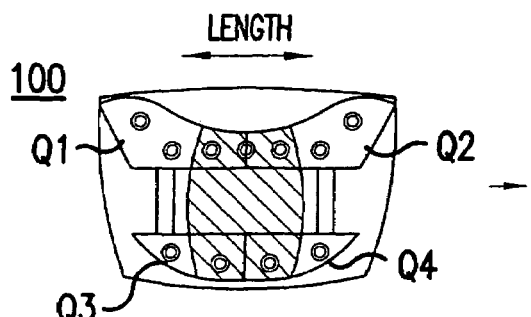
FIG. 2 illustrates ratcheting of the three-dimensional expansile total lumbar/thoracic titanium shells to conform to the length of the vertebral body (Embodiment I)
Figure 2B:
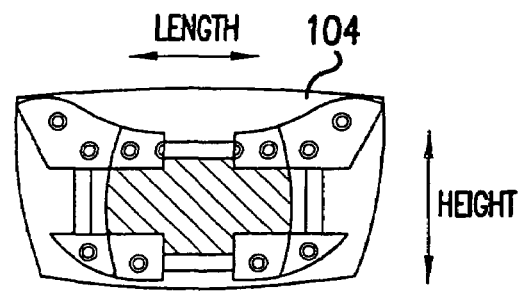

FIGS. 2A and 2B demonstrate ratcheting of the titanium shells Q1–Q4 to conform to the length of the lumbar/thoracic vertebral body 104.

Figure 3A:
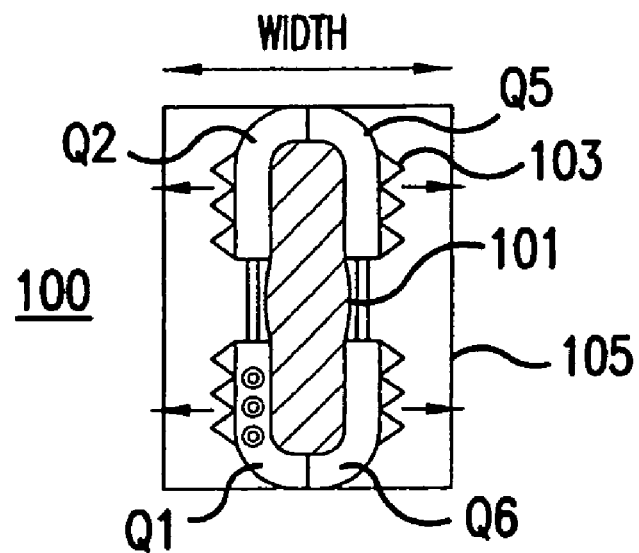
FIG. 3 illustrates the dorsal view of the three-dimensional expansile total lumbar/thoracic construct from the surgeon's perspective (Embodiment I)
Figure 3B:
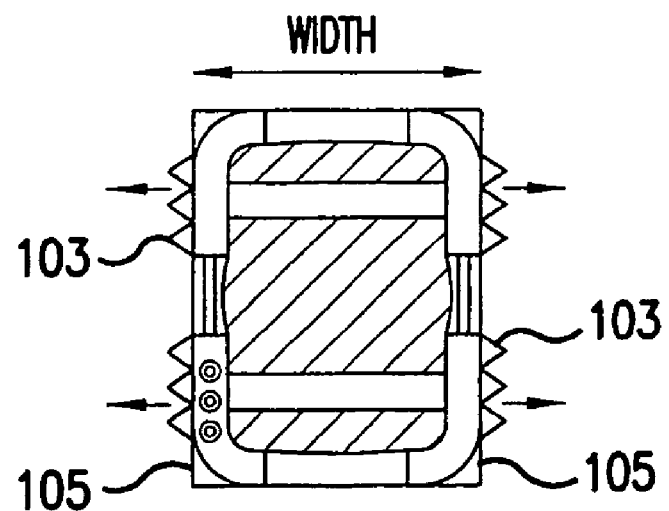

Once the construct 100 has been fine-tuned to conform to the height and length of the vertebral body 104, it can now be ratcheted to conform to the width of the disc space and to be secured to the endplates 105. FIG. 3A demonstrates the dorsal view of the construct 100 from the surgeon's perspective, upon initial placement of the construct. Note the expansile artificial disc core 101, two leaflets of titanium shells Q1, Q2, Q5, Q6 which are opposed to each other and the outer titanium spikes 103. Note the three screws 111, 112, 113. One of three screws ratchets the height of the implant (screw 111), another screw ratchets the length (screw 112), and another screw ratchets the width (screw 1133). FIG. 3B illustrates the width-expanded construct 100 accommodating to individual disc width, and titanium spike 103 endplate purchase.

FIGS. 4A–M illustrate the relationship of the screws to the internally incorporated expansion device 102 or cylinder-spur-gear-spring (CSGS) system allowing expansion of the prosthesis in all three planes. There are a total of three screws. 111, 112, 113. Any one screw controls the highly adjustable simultaneous movements of the appropriate titanium shells with respect to one another on both rostral and caudal leaflets, in any one given dimension (x, y or z). This is accomplished by internalizing and embedding within the titanium shells Q1–Q8 the expansion device 102 or the gear mesh, a cylinder-spur-gear spring (CSGS) system. This system is designed such that turning screw 111 adjusts the height of the prosthesis by moving the appropriate titanium shells in the z axis. Turning screw 112 adjusts the length of the prosthesis by simultaneously moving the appropriate shells in the x axis. Finally turning screw 113 leads to simultaneous expansion of the appropriate shells in the y axis. Turning screw 113 ensures the final locking position of the prosthesis by engaging and incorporating the outer spikes into the opposing rostral and caudal vertebral endplates.

Figure 4A:
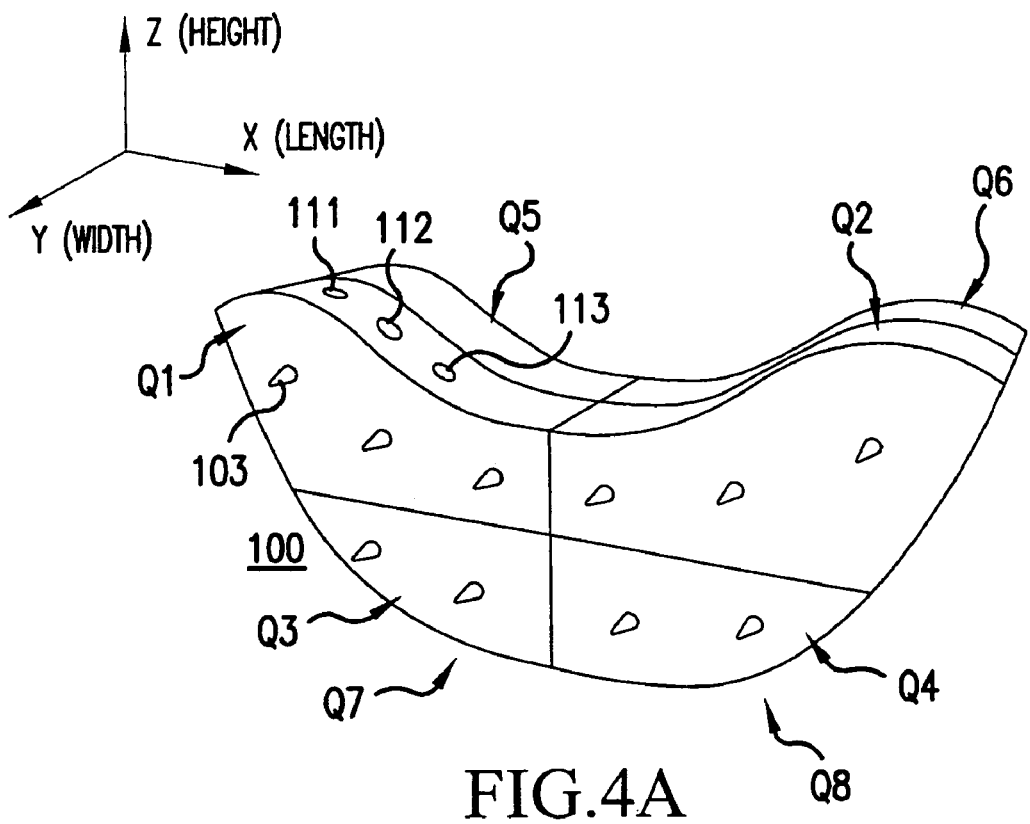

Referring now to FIG. 4A, a three dimension illustration of the lumbar/thoracic prosthesis 100 is provided, and it illustrates the three axes of motion (x,y, and z) vis-à-vis the interconnections between the superior/dorsal titanium shells (Q1, Q2, Q5, Q6) and the inferior/ventral shells (Q3, Q4, Q7, Q8), as well as the external surfaces of the titanium shells, as well as the external titanium spikes 103. It should be noted that screw 111 adjusts height; screw 112 adjusts length, and screw 113 adjusts width, and that during surgery, height, length and width screws 111, 112, 113 are sequentially adjusted. The titanium shells of FIG. 4A include rostral leaflet superior shells Q1, Q2; rostral leaflet inferior shells Q3, Q4; caudal leaflet superior shells Q5, Q6; and caudal leaflet inferior shells Q7, Q8.

Figure 4B:
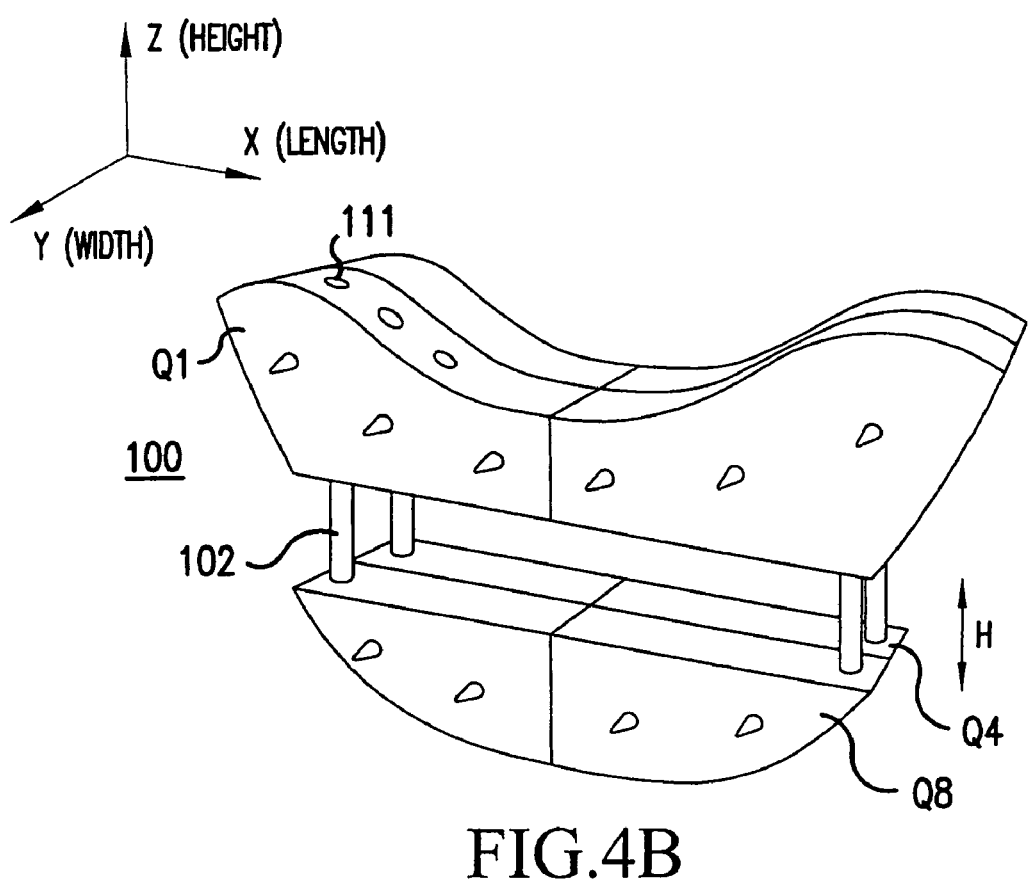

Referring now to FIG. 4B, an illustration of lumbar/thoracic prosthesis height and adjustment using screw 111 is provided. During a first stage of operation, screw 111 (height) is adjusted by counter-clockwise/clockwise twisting. The amount of turning of this screw 111 determines the device's resting height (H). It should be noted that in our Cartesian coordinate system, shell Q1 will always be fixed as a reference point (x=0,y=0,z=0). It should also be that noted the space between the shells Q1–Q8 is to be filed with a core 101 as explained in connections with embodiments I, II, III, IV, V. The core 101 is taken out of FIGS. 4a–4D to increase mechanical clarity.

Figure 4C:
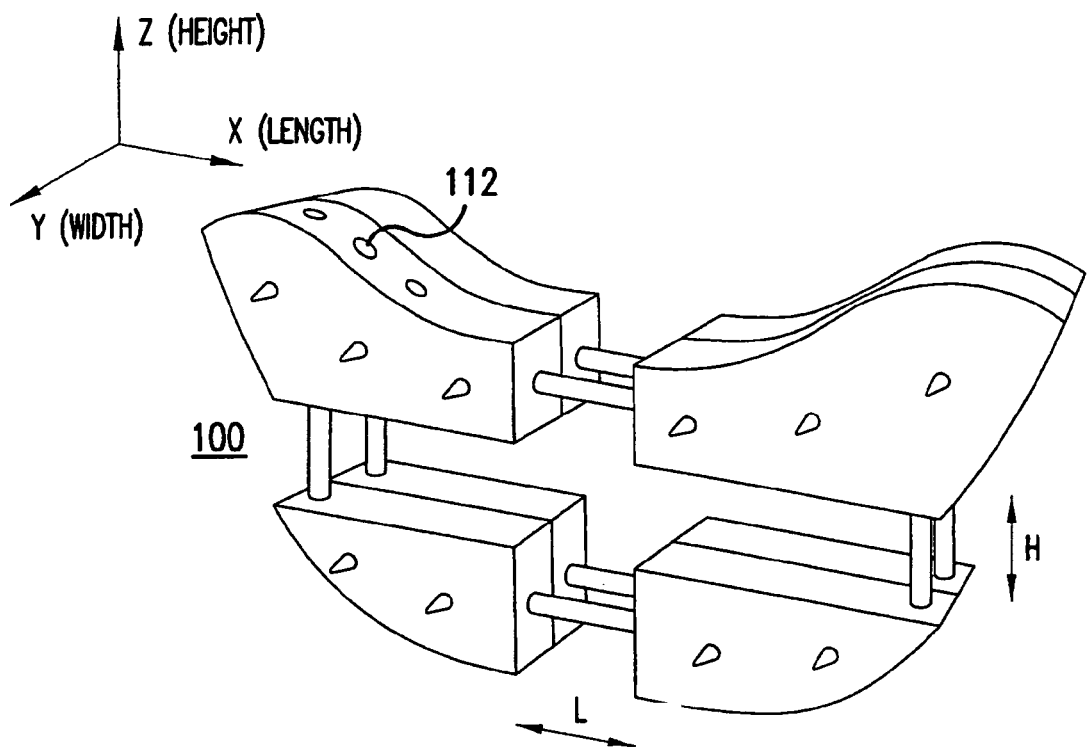

Referring now to FIG. 4C, a three-dimensional illustration of the lumbar/thoracic prothesis 100 is provided. The length (L) is adjusted with screw 112. During the second stage of operation, screw 112 (length) is adjusted by counter-clockwise/clockwise twisting. The amount of turning of screw 112 determines the device's final resting length.

Figure 4D:
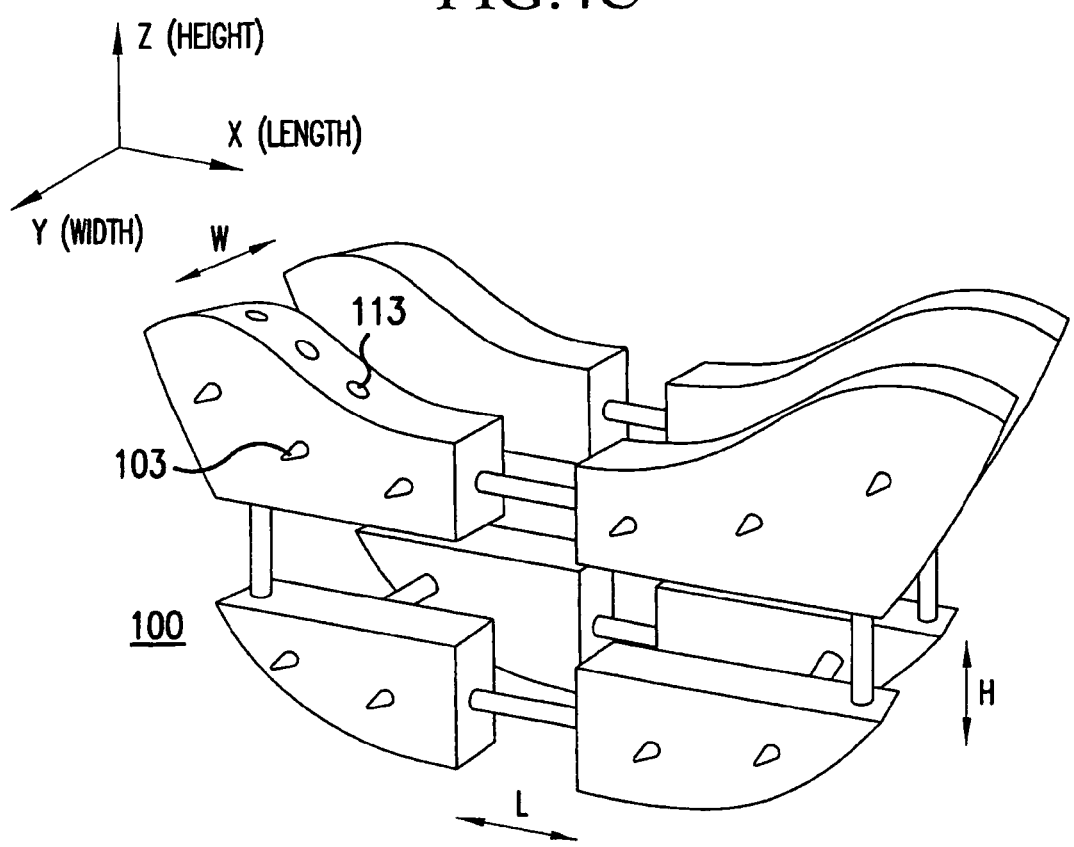

Referring now to FIG. 4D, a three-dimensional illustration of lumbar/thoracic prosthesis 100 is provided. The width (W) is adjusted screw 113. During the third stage of operation, screw 113 (width) is adjusted by counter-clockwise/clockwise twisting. The amount of turning of screw 113 determines the device's final resting width (W). This step is performed last, because the spikes 103 anchor into the bone.

Figure 4E:
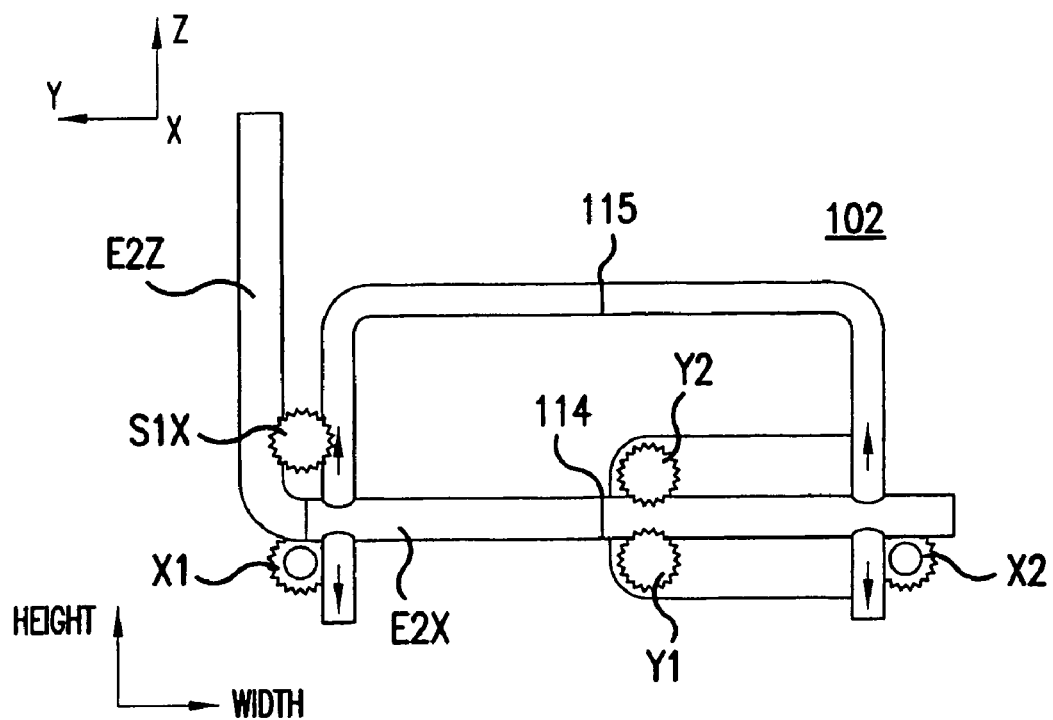

Referring now to FIG. 4E, a side view of the expansion device 102 controlled by the screws 111, 112, 113 is provided. The expansion device 102 includes a plurality of components. Component S1X rotates about the Y axis and moves along the Z axis. Component E2Z moves along the X axis. Component E2X rotates about the X axis, moves along the Y axis, and has spring connection 114 at its midpoint. Component X1 rotates about the X axis. Component Y1 rotates about X, and moves along the Y axis. Component X2 rotates about the Y axis. Component Y2 rotates about X, and moves along the Y axis. Component Z2 moves along the Z axis, and it has a ball-socket joint 115 at its midpoint. Component E2Z moves along the X axis.

Figure 4F:
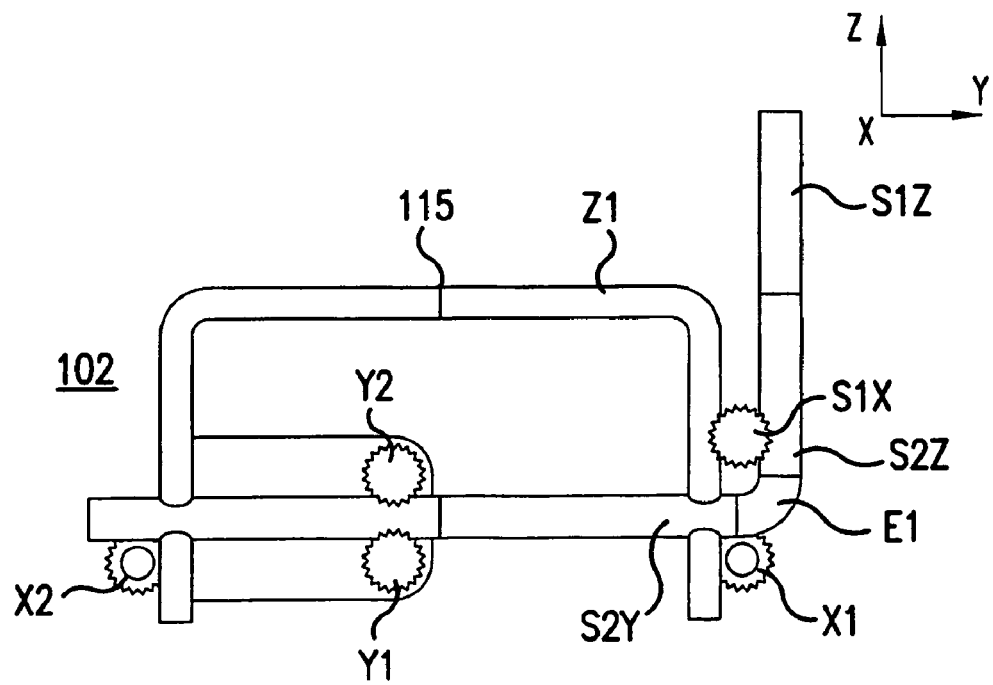

Referring now to FIG. 4F, a side view of the mechanical infrastructure of titanium shells Q1, Q3, Q5, Q7 is provided. Component Y2 rotates about X and moves along Y. Component Z1 moves along Z, has ball-socket joint 115 at its midpoint. Component S1Z rotates about Z. Component S1X rotates about X, and move along Z. Component S2Z rotates about Z. Component E1 is static with spring (not shown in diagram) connecting at midpoint along the width axis. Component S2Y rotates about Y. Component X1 rotates abut X. Component Y1 rotates about X and moves along Y. Component X2 rotates about X.

Figure 4G:
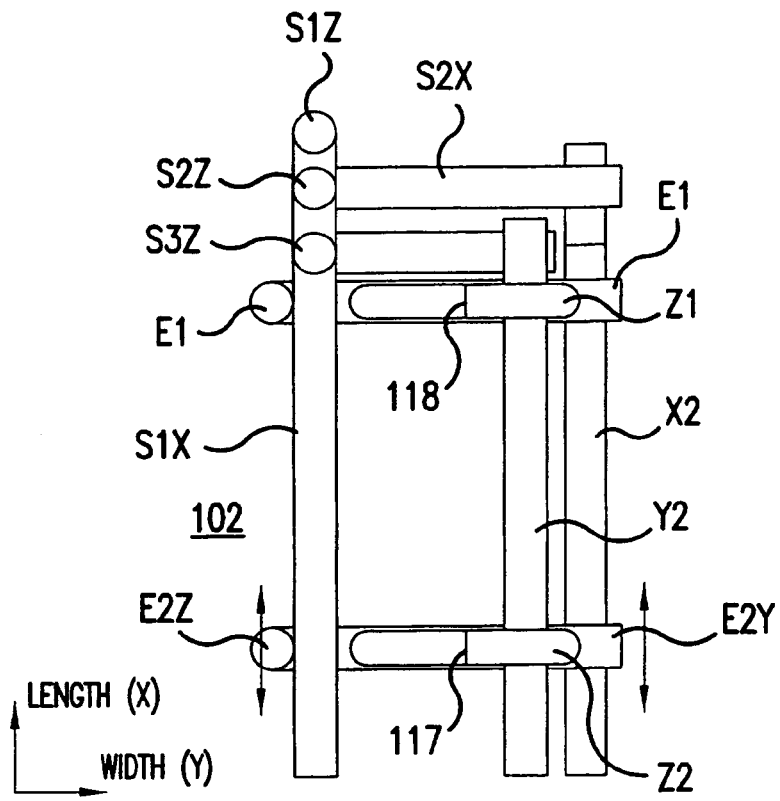

Referring now to FIG. 4G, a dorsal view of the mechanical infrastructure of titanium shells Q1, Q2, Q5, Q6 is provided. S1Z rotates about Z. Component S2X rotates about X. Component E1 is static with a spring (not shown in diagram) connecting at midpoint along the width axis. Component S3X rotates about Y. Component Z1 moves along Z, and it has a ball-socket joint 118 at its midpoint. Component X2 rotates about X. Component Y2 rotates about X and moves along Y. Component E2Y has rings that rotate about Y to force the structure to move along X. A coil spring is located at its midpoint. Component Z2 moves along Z and it has a ball-socket joint 117 at its midpoint. E2Z: Moves along X. Component S1X rotates about Y and moves along Z. Component E1 is static with spring (not shown in diagram) connecting at midpoint along the width axis. Component S3Z rotates about Z. Component S2Z rotates about Z.

Figure 4H:
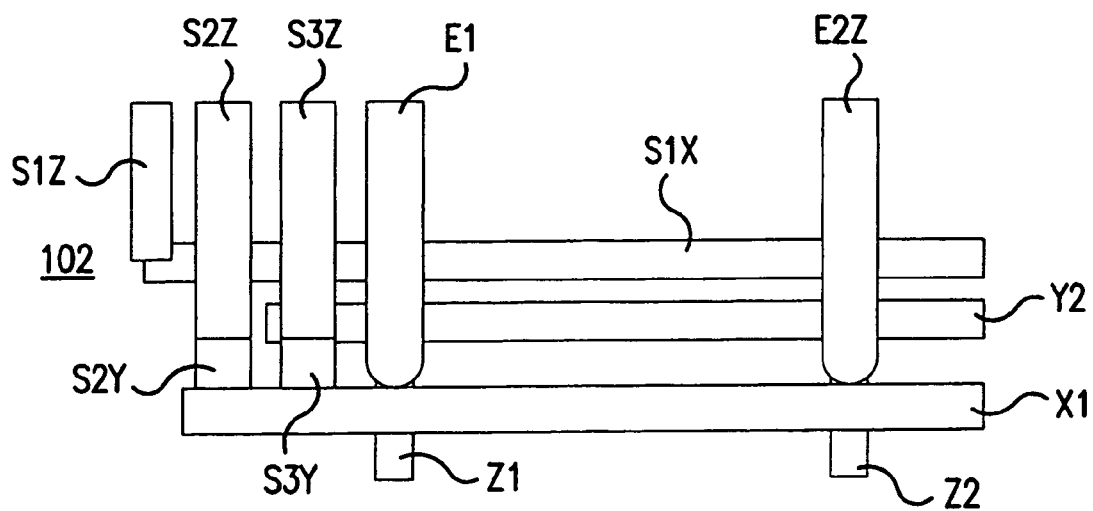

Referring now to FIG. 4H, a side view of the rostral titanium shells Q1, Q2, Q3, Q4 and the mechanical infrastructure is provided. Component S1Z rotates about Z. Component S2Z rotates about Z. Component S3Z rotates about Z. Component E1 is static with a spring (not shown in diagram) connecting at the midpoint along the width axis.

Component E2Z moves along X. Component Y2 rotates about X and moves along Y. Component X1 rotates about X. Component Z2 move along Z. Component S1X rotates about X and moves along Z. Component Z1 moves along Z. Component S3Y rotates about Y. Component S2Y rotates about Y.

Figure 4I:
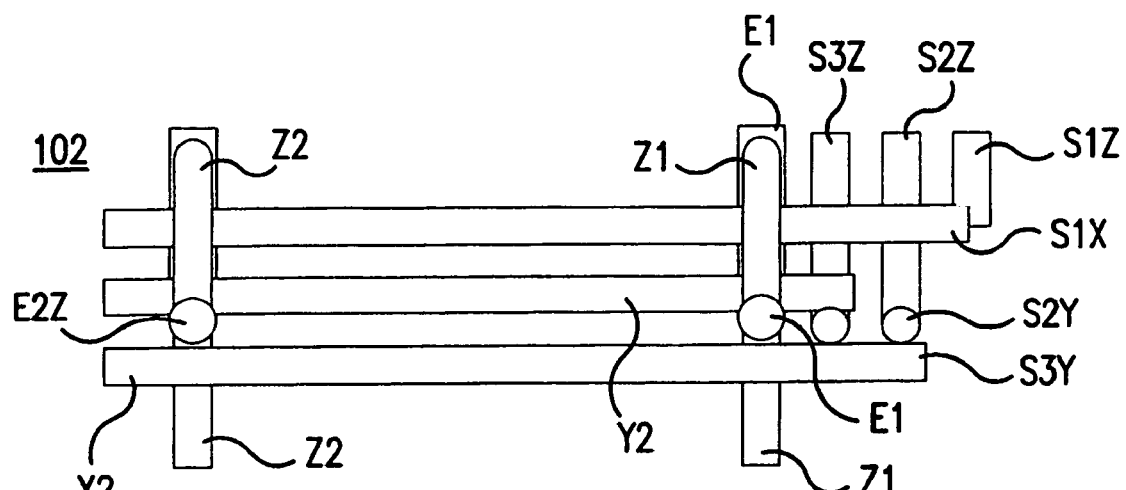

Referring now to FIG. 4I, an axial view of caudal titanium shells Q5, Q6, Q7, Q8 and the mechanical infrastructure is provided. Component E2Z rotates about Y and moves along X. Component Z2 moves along Z. Component Z1 moves along Z. Component E1 is static with a spring (not shown in diagram) connecting at the midpoint along the width axis. Component S3Z rotates about Z. Component S2Z rotates about Z. Component S1Z rotates about Z. Component S1X rotates about X and moves along Z. S2Y rotates about Y. S3Y rotates about Y. Component D1 is satic. Component Z1 moves along Z. Component Y2 rotates about X and moves along Y. Component Z2 moves along Z. Component X2 rotates about X and moves along Y.

Figure 4J:
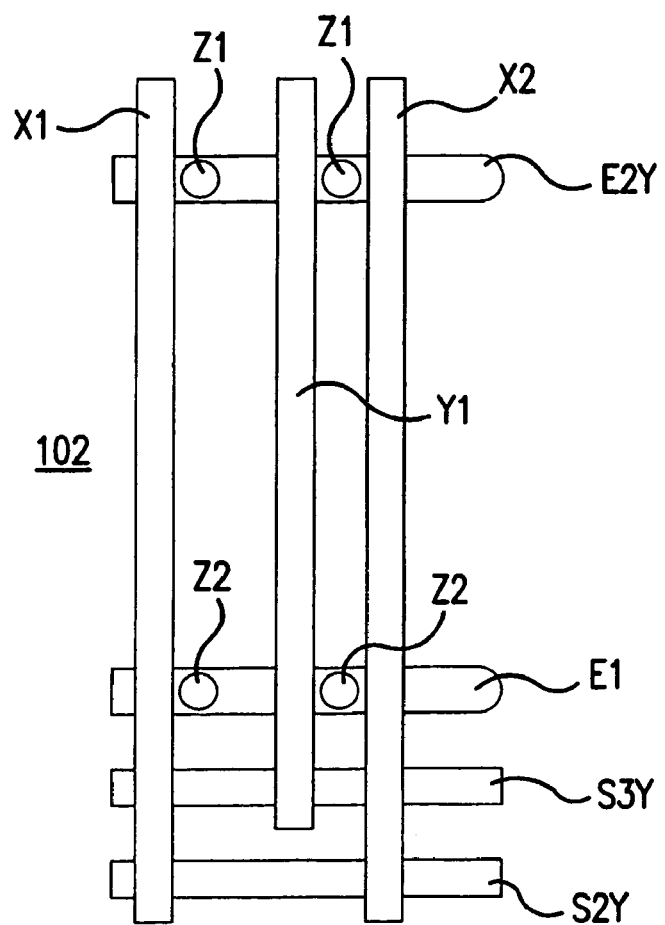

Referring now to FIG. 4J, a ventral view of titanium shells Q3, Q4, Q7, Q8 and the mechanical infrastructure is provided. Component X1 rotates about X. Component Z1 moves along Z. Component E2Y has rings that rotate about Y to force the structure to move along X. A coil spring is located at its midpoint. Component X2 rotates about X. Component Y1 rotates about X and moves along Y. Component Z2 moves along Z. Component E1 is static with a spring (not shown in diagram) connecting at the midpoint along the width axis. Component S3Y rotates about Y. Component S2Y rotates about Y.

Referring now to FIG. 4K, the mechnaical infrastructre and height adjustment components S1X, E2, Z2, E1, S1Z, Z1, Z2 are illustrated. In FIG. 4K(1), which provideds an overview of height adjustment system. Q3, Q4, Q7, Q8 are attached or linked to bottom pins as shown. Shells Q4 and Q8 are linked or connected to component Z2. Shells Q3 and Q7 are linked or connected to component Z1. FIG. 4K(2), shows how twisting of component S1Z (by external screw driver) about Z translates to a twisting of component S1X about X (via miter gears 121). Component S1Z is twisted by an external screw driver. Rotation of component S1Z causes rotation of component S1X by way of miter gears 121. In FIG. 4K (3), component S1X is held in space by components E1, E2, yet is allowed to twist about, interacting with the racks on component Z1 and component Z2 up or down along Z. Component S1X is held in space by a ring (that allows it to twist however) on both ends that are fixed to E1 or E2 (also by ring). Component Z1 is an upside-down letter-U shape that rises or lowers through holes in component E1. Component Z1 (and component Z2) has a rack on the left side of the U, as shown, to accommodate the complementary spurs on component S1X (in two locations). Since component S1X is held in place by component E2 (which is relatively static), component Z1 must move up (or down) when component S1X is twisted. Components E1, E2 are spring connected in their respective midpoints along the y(width) axis to allow for the Q1–Q2–Q3–Q4 complex to have three degrees of freedom with respect to the Q5–Q6–Q7–Q8 complex. Components Z1 and Z2 have ball-socket joints along their y(width) midpoints for this same reason. Components Z1, Z2 use ball sockets rather than aspring-coil in order to allow for uniform z-direction motion.

Referring now to FIG. 4L, the mechanical infrasructure length adjustment components E2, E1, S2Z, 2Y, X1, X2 are illustrated. In FIG. 4L(1), an overview is provided of the length adjustment mechanism. Shells Q2, Q4, Q6, Q8 are attached or linked to component E2. In FIG. 4L(2), component S2Z turns S2Y by miter gear (component S2Z is turned by an outside screw-driver). Component S2Z is twisted by an external screw driver. Rotation of component S2Z causes rotation of component S2Y by way of a miter gear. In FIG. 4L(3), component S2Y turns components X1, X2 by a bevel gear. Component S2Y interacts with component X1 through a bevel gear mechanism. Rotation of component S2Y causes rotation of component X1. In FIG. 4L(4), components X1 and X2 are threaded at the shown ends; their twisting caues the bevels surrounding E2 to move along the threading (in X). Components X1 and X2 have threaded sections at their ends, as shown, which when twisted force component E2 to move along the X-axis. Component E2 does not rotate at all, but has two threaded rings that are allowed to rotate in place in order to move component E2 along components X1, X2.

Referring now to FIG. 4M, the mechanical infrastructure and adjustment omponents E2, E1, S3Z, S3Y, Y1, Y2 are illustrated. In FIG. 4M(1), an overview of the widh adjustment mechanism is provided. Shells Q5, Q6 are attached or linked to Y1. Shells Q7, Q8 are attached or linked to component Y2. In FIG. 4M(2), the twisting of component S3Z by a screw driver turns component S3Y by a miter gear. Component S3Z is twisted by an external screw driver. Rotation of component S3Z causes rotation of component S3Y by way of a miter gear. In FIG. 4M(3), component S3Y is shown threaded at the end that touches component Y1 and component T2. Components Y1 and Y2 are spirally threaded in opposing directions so that both move in parallel along Y, either back or forth. Component Y1 has two intermediate spured sections, one corresponding to acomplementary rack on component E1, and the other to a complementary rack on component E2. Likewise, component Y2 has two spured sections. Both components Y1 and Y2 are beveled at their ends, as shown—in opposing diretions—one right-handed, the other left-handed. Component S3Y's rotation causes rotation in components Y1 and Y2, and thereby their parallel movements along the double racked components E1 (and E2).

Figure 5A:
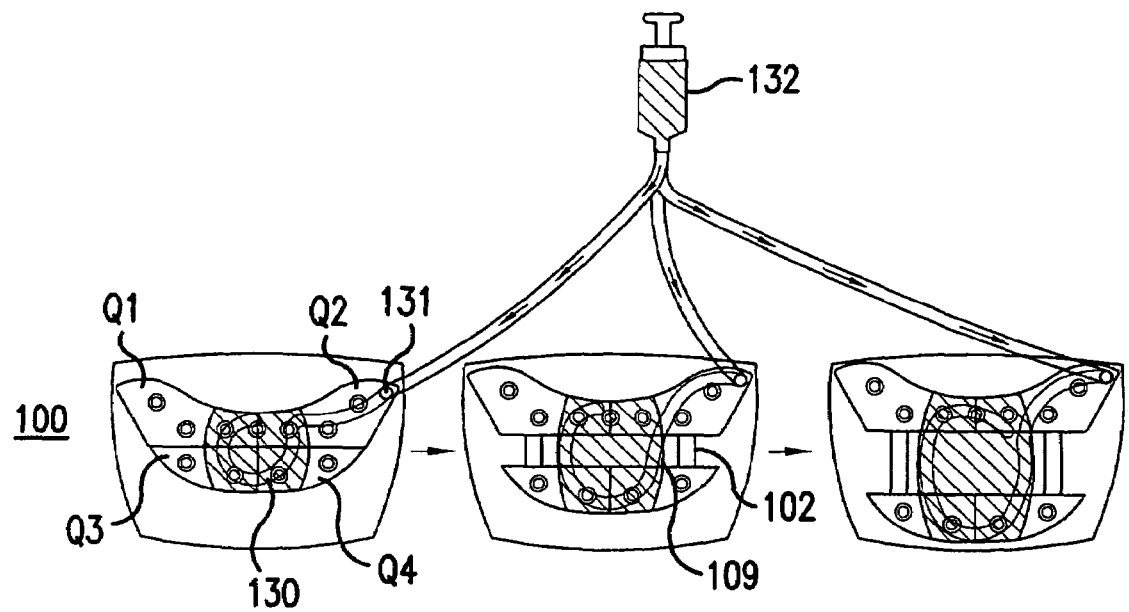
FIGS. 5A and 5B illustrate a second embodiment of the three-dimensional expansile lumbar/thoracic disc invention, i.e., these illustrate an in-situ injection/expansion elastic polymer nucleus design (Embodiment II)
Figure 5B:
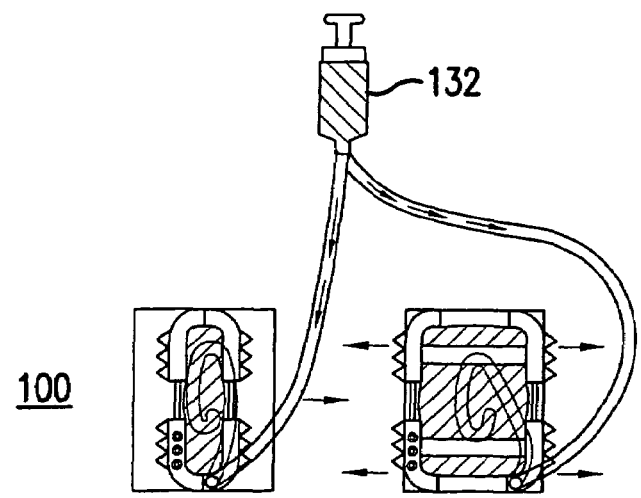

The present invention depends on an expansile disc core 101 that is molded to the titanium shells (Embodiment I). Rubber, silicon, or polyurethane variants are potential candidates for the core. Because there is already well-documented safe experience with elastic polyurethane, this would be the most likely candidate. One skilled in the art would need to select the most appropriate synthetic core, which has the physico-chemical properties of expansion upon release of pressure, while still maintaining elastic resilience Depending on the feasibility of finding and adapting a core with such properties, FIGS. 5A and 5B illustrate a second alternative embodiment (Embodiment II). FIG. 5A illustrates the first three stages of filling the device with an elastometric material, and FIG. 5B illustrates the final two stages. This design consists of the same boomerang shaped bi-leaflet with a total of eight ratchetable titanium shells Q1–Q8 in x, y and z planes. An expandable elastometric sheath 109 is molded to the shells, and can enlarge and conform to the disc space. Within this sheath is a coil 130 with pores (micro-catheter) attached to a port 131. Once the titanium shells Q1–Q8 are fine tuned to the height and length of the vertebral body, and the width fine tuned to the disc space, liquefied material can be injected into this port 131 from a source 132 filling the elastometric balloon 109 until it fills the disc space and conforms to its geometry, as illustrated in FIG. 5B. It then cures (gels) permanently. This material could include polycarbonateurethane, polyurethane, polyvinyl alcohol, protein hydrogel, or any other material that one skilled in the art might select. The previous safe employment of protein hydrogel and polyurethane in nucleus disc cores makes these materials the most likely candidates. The appropriate selection of cores with specific chemico-physical properties is a significant design choice.

FIGS. 6A, 6B and 6C illustrate a third alternative embodiment (Embodiment III). This embodiment is an expansile, custom-fit, mechanical metal on metal, ball on trough design (FIG. 6A). It consists of two leaflets, rostral and caudal, 140 and 141. Each leaflet 140, 141 in turn consists of three shells; 1) An inner stainless steel shell 142 with a trough on the rostral leaflet, or with a protruding steel ball 143 on the caudal leaflet, 2) An intermediate thin titanium plate 144 or 145 which is molded to the outer surface of the stainless steel shells 142, 143, and to the inner surface of the outer moveable titanium shells Q1–Q8, and 3) Outer titanium shells Q1–Q8, four on each leaflet, which when ratcheted glide over the intermediate titanium plates 144, 145 allowing expansion of prosthetic height and length to conform i.e. custom fit to the individual vertebral endplate.

FIG. 6B(1) illustrates an axial composite view of the lumbar/thoracic metal on metal, ball on trough prosthesis 100. It illustrates the horizontal and vertical movements of the four titanium shells Q1–Q4 per leaflet expanding in height and length conforming to the particular vertebral body dimensions.

FIGS. 6B(1)–6B(3) illustrate different positions of the inner and outer surfaces of each of the separate three shells per leaflet, which mechanically allow expansion of the implant in x, y, and z dimensions while maintaining a static relationship between the metal on metal ball and trough. FIG. 6C(1) illustrates the outer surface of the outer titanium shells Q1–Q4. It has spikes 103 to engage the vertebral endplates, with four moveable shells as mentioned in the two other designs above. FIG. 6C(2) illustrates the inner surface of the outer titanium shells Q1–Q4. It has both horizontal and vertical bar elevations which fit into horizontal and vertical grooves 150, 151 of the outer surface of the intermediate titanium shells 144, 145. This is the mechanism, which allows height and length prosthesis extension. Also note the cross section of four ratchetable bars 152 which extend from the intermediate titanium shell 144 to the outer surface of the inner stainless steel shell 142 allowing expansion of prosthetic disc width, while maintaining static contact between the inner surfaces of the stainless steel ball and trough.

FIG. 6C(4), illustrates the inner surface 153 of the intermediate titanium shell 144. This is molded to the outer surface of the inner stainless steel ball and trough shells 142, 143. Also note the cross-section of the four width expansion bars 152.

FIGS. 6C(5) and FIG. 6C(6) illustrates the inner surfaces of the inner stainless steel shells 142, 143. The rostral leaflet has a depression 154, i.e. a trough, serving as a socket for the steel ball 155 of the opposing leaflet. FIG. 6C(7) illustrates the outer surface of the inner stainless steel shells 142, 143. This is molded to the inner surface of the intermediate titanium shell 144. Also note the cross-section of ratchetable bars 152 allowing width expansion.

FIGS. 7A(1)–7A(2) illustrate a fourth alternative embodiment of the lumbar/thoracic design (Embodiment IV). This embodiment is an expansile, custom-fit, mechanical metal on metal, biconvex ultrahigh molecular weight polyethylene (UHMWPE) design. It consists of two leaflets 161, 162, rostral and caudal. Each leaflet in turn consists of three shells; 1) An inner UHMWPE convex shell 163, 2) An intermediate thin titanium plate 164 which is molded to the outer surface of the UHMWPE shell 163, and to the inner surface of the outer moveable titanium shells Q1–Q8, and 3) Outer titanium shells Q1–Q8, four on each leaflet which when ratcheted glide over the intermediate titanium plate 164 allowing expansion of the prosthetic height and length to conform, i.e. custom fit to the individual vertebral endplate. FIG. 7A(2) illustrates the width adjustment of the fourth alternative embodiment.

FIGS. 7B(1)–7B(3) illustrate an axial composite view of the lumbar/thoracic metal on metal, biconvex UHMWPE prosthesis. It illustrates the horizontal and vertical movements of the four titanium shells Q1–Q4 of one leaflet expanding in height and length conforming to the particular vertebral body dimensions.

FIGS. 7C(1) and 7C(2) illustrate the axial views of the outer and inner UHMWPE biconvex shell 163 surfaces. The axial views of the outer and inner surfaces of the outer titanium shells Q1–Q8 are identical to those illustrated in FIGS. 6C(1) and 6C(2). The axial views of the outer and inner surfaces of the intermediate titanium shell is identical to that illustrated in FIGS. 6C(3) and 6C(4).

FIGS. 8A and 8B illustrate a fifth alternative embodiment of the lumbar/thoracic disc (Embodiment V). This embodiment is an expansile, custom fit, mechanical metal on metal, monoconvex UHMWPE design. It consists of two leaflets 171, 172, rostral and caudal. The rostral leaflet consists of two shells; 1) an inner thin titanium shell 173 which is molded to the inner surface of the 2) outer titanium shells Q1–Q4. The caudal leaflet has three shells; 1) An inner monoconvex UHMWPE shell 174, 2) An intermediate thin titanium plate 175 which is molded (vulcanized) to the outer surface of the UHMWPE shell and to the inner surface of the outer moveable titanium shells Q1–Q4, and 3) Outer titanium shells Q1–Q8, four on each leaflet, which when ratcheted glide over the intermediate titanium plates 173, 174 allowing expansion of the prosthetic height and length to conform, i.e. custom-fit to the individual vertebral endplate. The composite axial view of the total lumbar/thoracic metal on metal, monoconvex UHMWPE disc (Embodiment V) is identical to that illustrated in FIGS. 7B(1)–7B(3) (UHMWPE biconvex embodiment, IV). The cross-sectional axial views of the outer and inner surfaces of the outer titanium shells for both rostral and caudal leaflets (Embodiment V) is identical to that illustrated in FIGS. 6C(1) and 6C(2). The axial views of the outer and inner surfaces of the intermediate titanium shell of both rostral and caudal leaflets for Embodiment V is identical to that illustrated in FIGS. 6C(3) and FIG. 6C(4). The axial views of the inner and outer surfaces of the monoconvex UHMWPE shell of the caudal leaflet are identical to FIGS. 7C(1) and 7C(2). There is no equivalent UHMWPE shell on the rostral leaflet.

FIG. 9A illustrates a total Lumbar/Thoracic prosthetic disc 200, which expands in two instead of three dimensions. The prototype used to illustrate this design is a variant of the psedoannulus three dimensional designs employed in embodiments I–V. In this embodiment (VI) there are a total of four titanium shells Q'1–Q'4. There are two dorsal shells Q'1, Q'2 (rostral and ventral), and two caudal (rostral and ventral) shells Q'3, Q'4. There is a single widened bar 220 attaching the dorsal and ventral shells Q'1–Q'4 which expands the height by ratcheting two screws 221 for either rostral or caudal height control.

FIGS. 9B(1) and 9B(2) illustrate the dorsal surgeon's view. Note the central width bar 224 which connects the rostral and caudal titanium shells Q'1–Q'4 dorsally and ventrally. Ratcheting the central screw 225 expands the dorsal width driving the dorsal rostral and caudal shell titanium spikes 203 into the vertebral bodies. Ratcheting a ventral central width screw (not shown) widens the ventral rostral and caudal shells Q'3, Q'4 leading to engagement of spikes 203 into the bone. This screw can be accessed endoscopically as will be described below.

FIG. 9C(1) illustrates an oblique view of the rostral and caudal shells Q'1 and Q'2 and the width expansion bar 224 and ratchet screw 225. FIG. 9C(2) illustrates an oblique view of the rostral and caudal shells Q'3 and Q'4 and the width expansion bar 228 and ratchet screw 229.

FIG. 9D(1)–9D(3) illustrates an enlargement of the width widening bar 224. It consists of an inner bar 231 with corrugations, which is in contact with inner grooves of the outer bar 232. By ratcheting the screws 233, 234 in the clockwise direction, width expansion is achieved. By ratcheting the screws 233, 234 counter clockwise, width contraction is achieved. Prosthesis width expansion allows incorporation of the spikes 203 into the bone. Once the spikes have engaged the bone to achieve maximal expansion, screws 233, 234 can now be turned counter clockwise. This will lead to the contraction of the inner width bar 231 within the outer width bar 232, enabling the removal of these bars from the construct. Now that the spikes 203 have engaged the bone, removal of the bars are important for allowing complete and uninhibited flexibility of the prosthesis in this most important dimension.

Figure 9E:
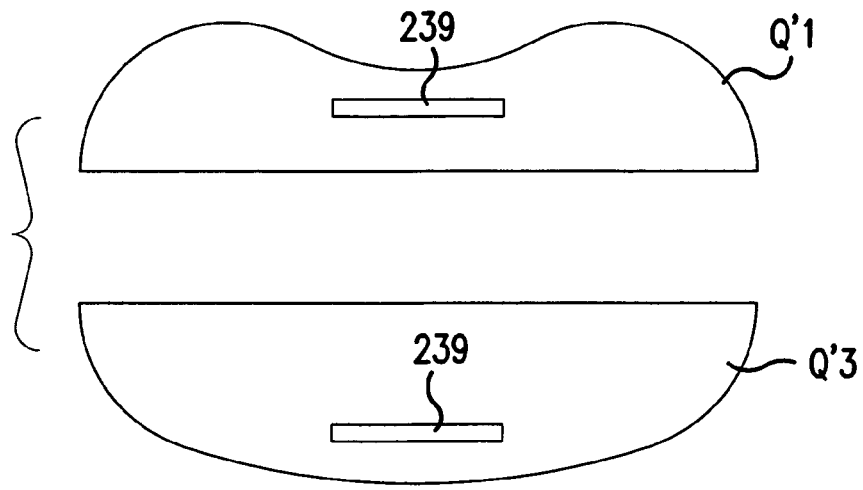

FIG. 9E illustrates the axial view of the inner surfaces of the dorsal and ventral titanium shells Q'1 and Q'3 revealing the indented grooves 239 into which the width bars 224, 228 is inserted, and expanded. When the width bars 224, 228 are contracted, the bars fall away from these grooves 239 facilitating their removal.

This two-dimensional pseudo annulus variant (embodiment VI) can be combined with the same cores described for embodiments I, I, III, IV and V. Thus the cores used in embodiments I–V can be adapted and combined with a pseudo annulus which can expand in two or three dimensions. To compensate for the lack of length expansion of the two-dimensional design, it would become necessary to design this variant with the appropriate range of differing length options.

FIG. 10A1 illustrates a perspective of a total lumbar/thoracic prosthetic disc pseudo annulus 1000 (Embodiment VII) which expands in two dimensions. The prosthetic disc 1000 includes four shells 1111, 1112, 1113, 1114, and a plurality of spikes 1115. FIG. 10A2 illustrates a simplified perspective view of the prosthetic disc 1000 and a pair of jackscrew width expansion mechanisms 1022. Screws 1005, 1006 control the jackscrews 1021, 1022 respectively. FIG. 10A3 is a perspective view that illustrates the jackscrews 1021, 1022 and two fixed-screw height expansion mechanisms 1023, 1024 which are controlled by screws 1001, 1002, 1003, 1004. This Embodiment VII can also be combined with either of the cores of embodiments I, II, III, IV or V.

Figure 10B:
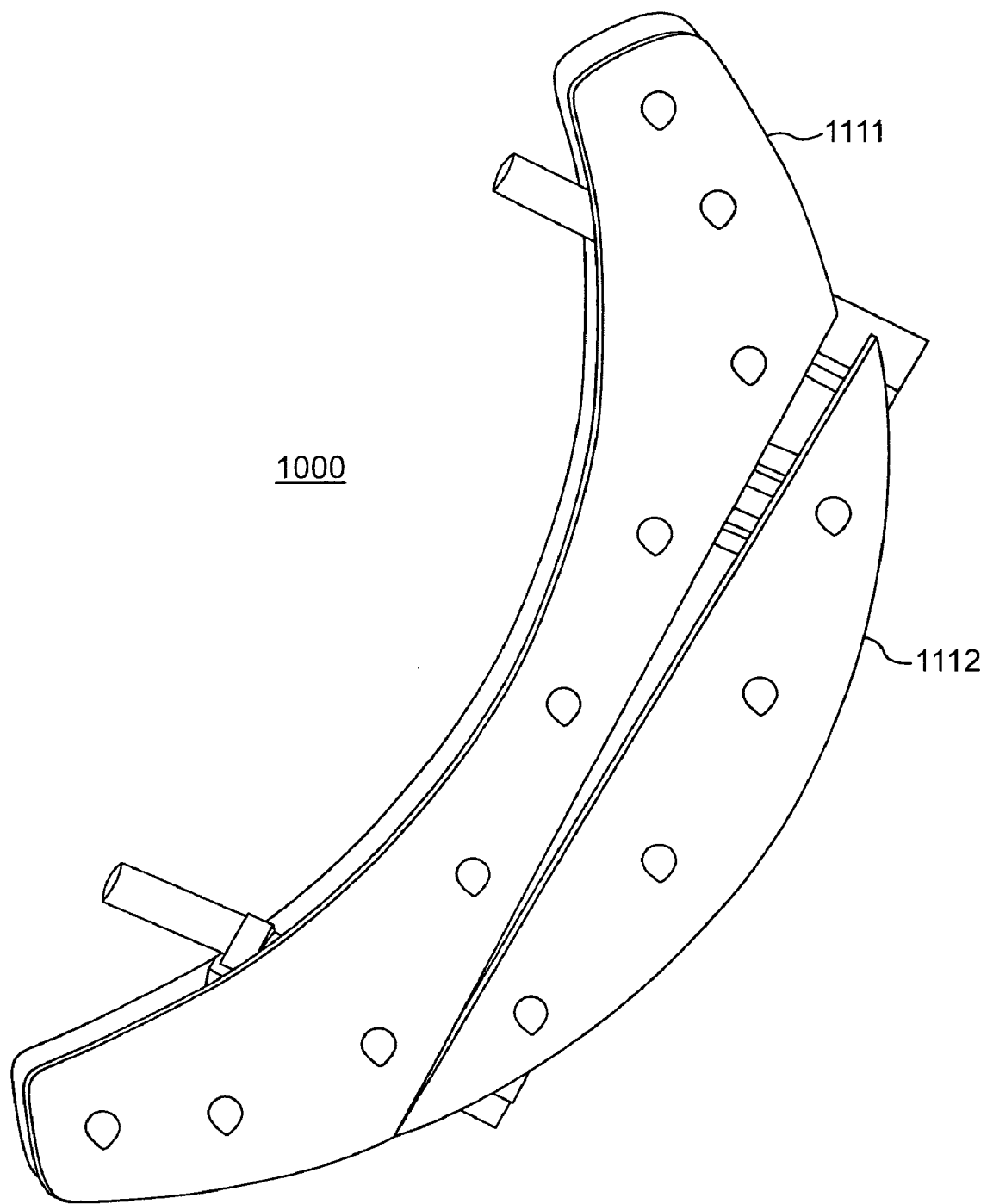

FIG. 10B illustrates a side view of the prosthetic disc 1000 that sequential turning of screws 1001, 1002, 1003, 1004 leads to height expansion of the rostral and caudal shells 1111, 112 by widening the distance between their superior and inferior shells.

Figure 10C:
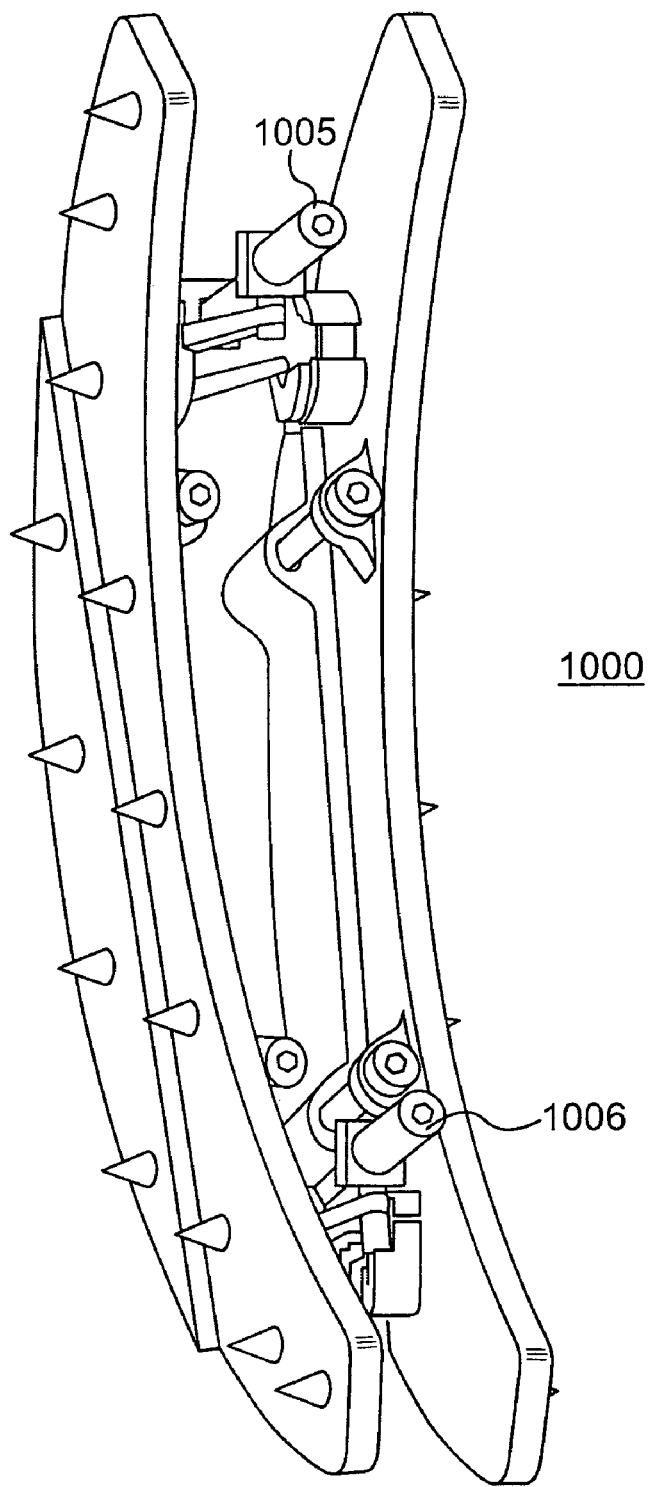

FIG. 10C illustrates that turning screws 1005, 1006 leads to width expansion of the prosthesis 1000 by widening the distance between the rostral and caudal superior and inferior shells 1111–1114.

Figure 10D:
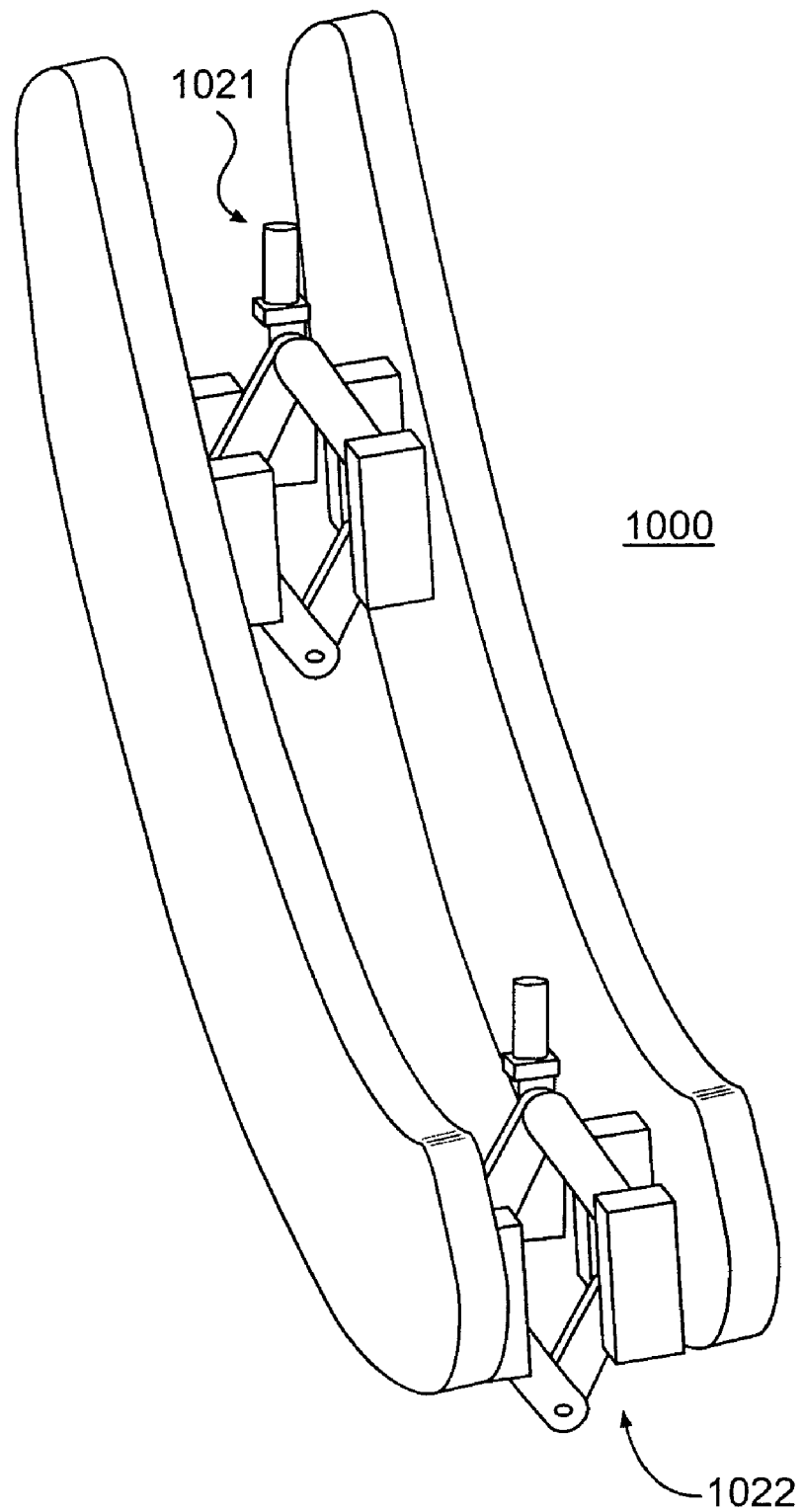

FIG. 10D illustrates an enlarged simplified perspective view of the jackscrew width expansion mechanisms 1021 and 1022.

Figure 10E:
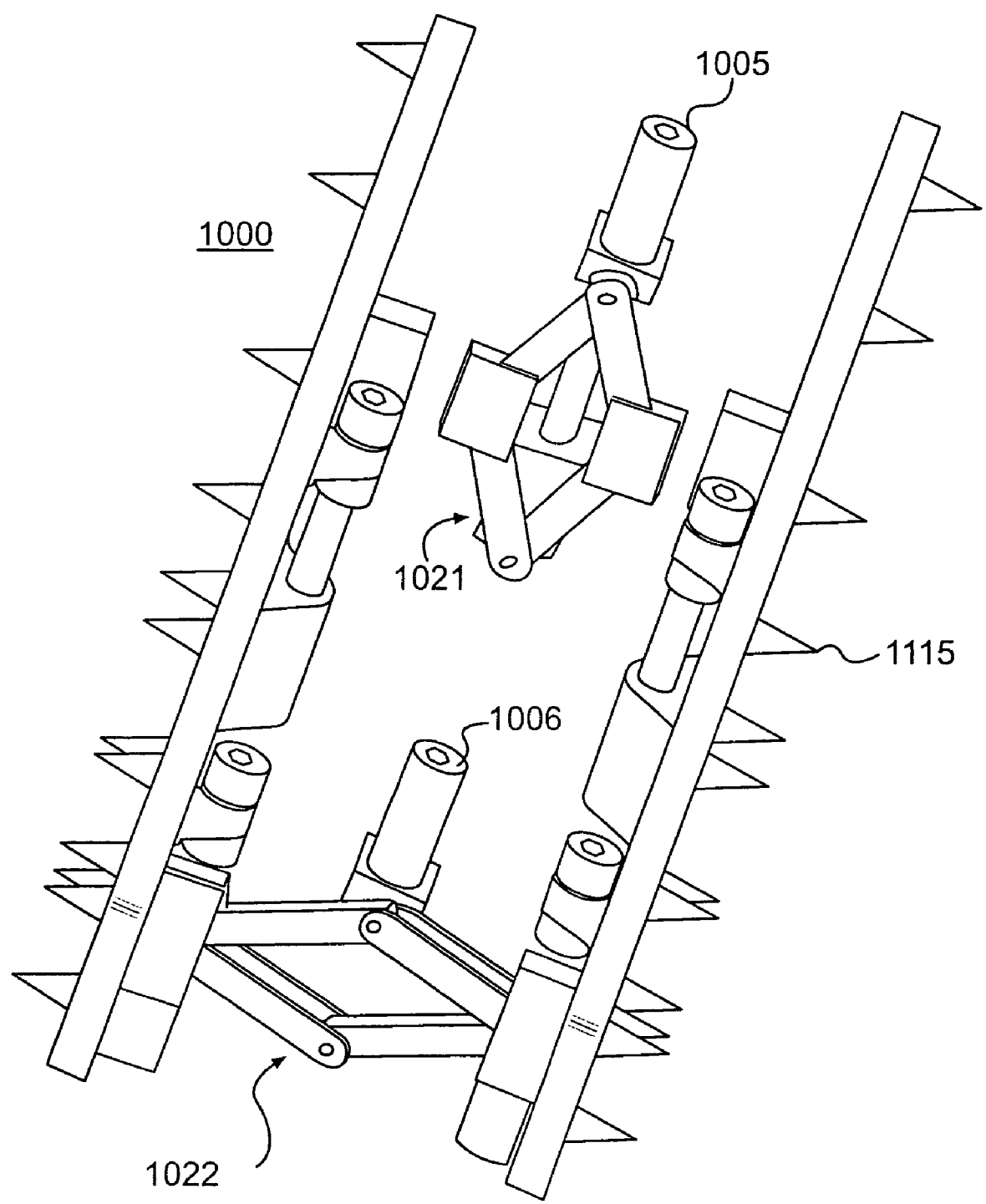

FIG. 10E illustrates that once maximum width expansion of prosthetic disc 1000 and purchasing of spikes have been achieved, the jackscrews 1021 and 1022 can be removed by counter turning screws 1005 and 1006. Removal of these screws 1005, 1006 allows unconstrained or semi constrained motion of the prosthetic device 1000 depending on which core is selected to be inserted into this pseudo annulus embodiment.

FIGS. 11A1–11A6 illustrate the basic jackscrew 1021 opening and closing mechanism of embodiment VII. Illustrated is the geometric conformation the jackscrew 1021 assumes enabling expansion of the rostral and caudal shells 1111–1114, and the conformation it assumes allowing its removal. As illustrated in FIG. 11A3, the more horizontally aligned the four arms 1031–1034 of the jackscrew 1021 are the greater the expansion. As illustrated in FIG. 11A5, the more vertically oriented the four arms 1031–1034 of the jackscrew 1021 are the greater the contraction.

FIG. 11B1–11B6 illustrate the mechanism of mechanical opening and closing of the jackscrew 1021 (embodiment VII). A straight screw 1005 is attached to the superior and inferior central apices of the jackscrew 1021. Turning the screw 1005 counterclockwise leads to horizontally oriented expansion/lengthening of the jackscrew 1021 arms which are attached to the titanium shells 1111–1114 achieving device expansion. Turning the straight screw 1005 clockwise leads to vertically oriented contraction/shortening of the jackscrew arms 1031–1034 allowing the jackscrew 1021 to be detached from the titanium shells 1111–1114 upon final engagement of the shells' titanium spikes.

FIG. 11C1–11C6 illustrates a mechanism for sequential electrical opening and closing of the jackscrew 1021 employed in embodiment VII. As illustrated in FIG. 11C2, two partially insulated wires 1041, 1042 (e.g. nitinol) are embedded into the jackscrew 1021. One vertically oriented wire 1041 is attached to the superior and inferior jackscrew apices 1043, 1044. Another horizontally oriented wire 1042 is attached to the rostral and caudal jackscrew apices 1045, 1046. When power is applied to the vertical wire 1041 from the power supply 1050 by activating the switch the four arms of the jackscrew 1021 contract achieving more horizontally oriented positions thereby expanding the device. When power is applied to the horizontal wire 1042, the four arms of the jackscrew 1021 achieve a more vertical position thereby leading to contraction of the device. The jackscrew 1021 can then be removed as illustrated in FIG. 11C6. The electrical jackscrew 1021 can be controlled by an external power source 1050 making it wire controlled. Alternatively the power source can be enclosed in the jackscrew 1021 itself making it a wireless device. If desirable the same electrical jackscrew mechanism 1021 may be employed for vertical height expansion of the embodiments as well.

FIGS. 11D1–11D6 illustrates a hybrid mechanical-electrical mechanism to expand and contract the jackscrew 1021 of embodiment VII. This design employs the placement of a vertical screw 1005 as well as a vertically oriented insulated wire 1041 attached to the superior and inferior apices of the jackscrew 1021. It also has a horizontally oriented insulated wire 1042 attached to the rostral and caudal apices of the jackscrew 1021. The purpose of this design is to have a mechanical backup in the event of an electrical failure/malfunction. The power from a power supply 1050 applied can be external to the jackscrew 1021 making it wire controlled, or it could be enclosed in the jackscrew 1021 making it wireless controlled.

a. The Surgical Method

The surgical steps necessary to practice the present invention will now be described.

For posterior lumbar spine prosthetic implantation there are two embodiments of the surgical approach: A) Classic microscopic open lumbar hemilaminotomy and discectomy, and B) Minimally invasive microendoscopic hemilaminotomy and discectomy.

Classic Microscopic Open Hemilaminotomy/Discectomy (Approach A):

Step 1. After the adequate induction of general anesthesia, the patient is placed prone on a radiolucent Jackson table. The patient is prepped and draped and using x-ray or fluoroscopic guidance, the correct disc space is identified. The microscope is brought in for appropriate magnification of the operative site. A routine hemilaminotomy is performed as fully described elsewhere.

Figure 12A:
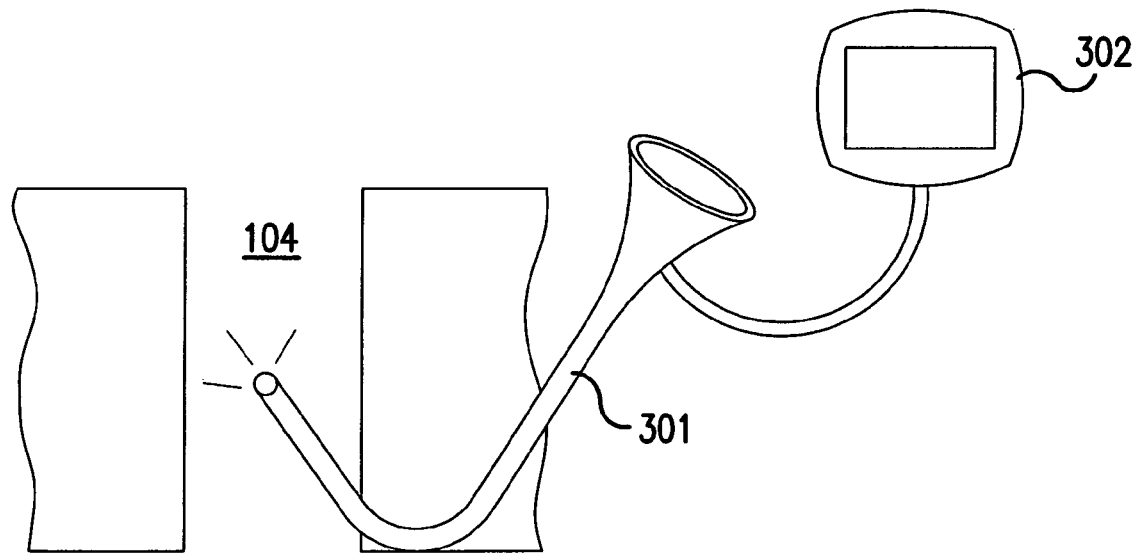
FIG. 12A represents an endoscope variant of the present invention inserted unilaterally into the disc space to inspect the disc space circumferentially.
Figure 12B:
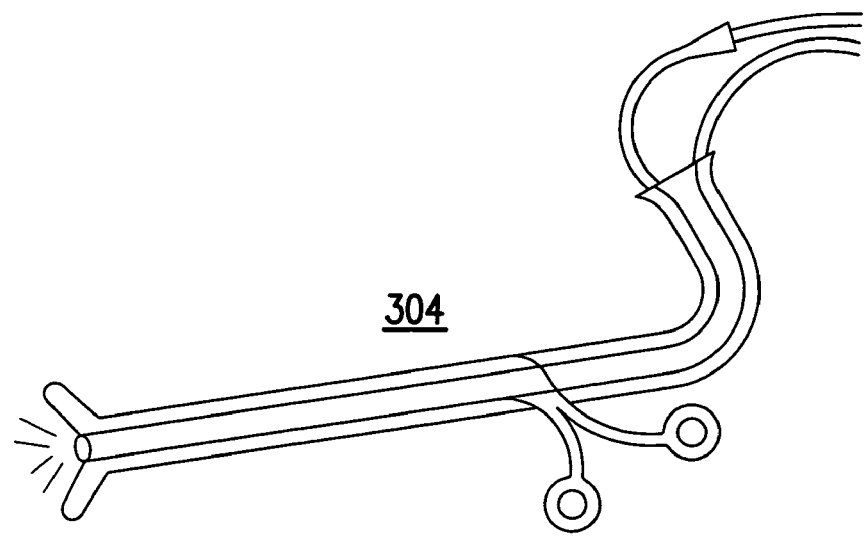
FIG. 12B represents a specifically designed pituitary rongeur endoscopic attachment with a light source emanating from the junction of the adjoining dorsal and ventral cup forceps. This significantly aids in performing a complete circumferential discectomy necessary for adequate prosthesis implantation.
Figure 12C:
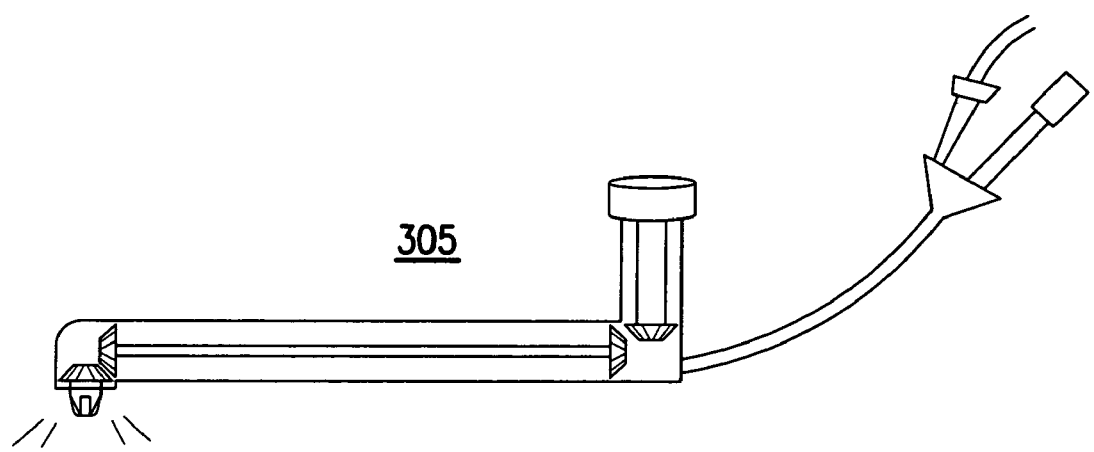
FIG. 12C illustrates a right-angled ratchet driver integrated into an endoscope to assist in visualization of screws beneath the caudal aspect of the spinal cord or thecal sac, if necessary.

Step 2. A complete discectomy is performed, and the endplates are curetted thereby preparing the disc space for prosthesis implantation. An endoscope can be employed to verify from a unilateral hemilaminotomy a successful circumferential discectomy. FIG. 12A illustrates an endoscope variant of the present invention having an endoscope 301 and a monitor 302 that specifically looks into the disc space 104 (discoscope) to verify an adequate circumferential discectomy. FIG. 12B illustrates a specifically lightweight design pituitary rongeur endoscopic 304 attachment, which can also be used to assist in complete and adequate discectomy for prosthesis implantation. A specifically designed right-angled screw ratcheter endoscopic attachment 305 can be used to aid in visualization and ratcheting of screws if partially hidden by the spinal cord ortheal sac as in FIG. 12C.

Step 3. The boomerang shaped artificial lumbar/thoracic disc, embodiment I, II, III, IV, V or VI is unilaterally inserted into the disc space by gently retracting the thecal sac and nerve root, and using a forceps or a similar specifically designed instrument to grab and secure the device. Once the edge of the boomerang is introduced into the disc space, it is then curvalinearly further inserted into the disc space underneath the thecal sac and nerve root, aligning the horizontal axis of the prosthesis with the horizontal axis of the vertebral endplate.

Step 4. Once the construct is beneath the thecal sac, using live fluoroscopy, adjust (ratchet) the construct height (Screw 1) until the outer titanium shells conform to the individual vertebral endplate height. Specifically designed screwdrivers, straight or right-angled, of appropriate length and screw fittings are employed.

Step 5. Now again using live fluoroscopy adjust (ratchet) the length of the titanium shells until the prosthesis conforms to the desired individual length of the vertebral body (Screw 2). In embodiments VI and VII there are no length adjustments. Measurements of the length of the vertebral bodies will determine the selection of prefabricated prostheses of different lengths.

Step 6. Now under direct microscopic or endoscopic visualization adjust (ratchet) the prosthesis width screw. As the width is expanded conforming to the precise disc width, the titanium outer spikes will engage, and then penetrate the bony endplates. Once total spike-bone penetration has occurred with complete purchase of the spikes, the implant is now safely secured in its position, and custom fit with respect to all x, y and z planes. Final lateral and anterior-posterior fluoroscopic images are then obtained to verify the precision fit. Verification of prosthetic purchase to the endplates can be performed by grasping and testing the prosthesis with a forceps verifying lack of motion. For Embodiment VI, once width expansion has been achieved, and the spikes 200 incorporated into the bone, the width bars 224, 228 are removed by turning screws 225, 229 counter clockwise (see FIGS. 9C(1) and 9C(2)). For embodiment VII once width expansion has been achieved the jackscrews are removed (see FIGS. 10E and FIGS. 11A, 11B, 11C AND 11D)).

Posterior Lumbar Minimally Invasive Microendoscopic Lumbar Hemilaminotomy (Approach B).

Step 1. After the adequate induction of general anesthesia the patient is placed prone on a radiolucent Jackson table. The patient is prepped and draped. Then using fluoroscopic guidance a minimally invasive microendoscopic approach is used to gain access to the appropriate disc space as described in detail elsewhere. In brief, serial tubular dilators are sequentially placed in the dorsal musculature and fascia through which a working channel is created and an endoscope is docked on the appropriate laminar landmark.

Step 2. Through the working channel a discectomy is performed. The endoscope can be repositioned to verify complete discectomy.

Steps 3–6 are then performed identically to steps 3–6 mentioned above (Approach A; Posterior lumbar placement using an open classical microscopic technique).

The steps for anterior implantation of lumbar/thoracic prosthetic devices, embodiments I, II, III, IV, V, VI or VII into the lumbar L4/5 and L5/S1 disc interspaces will now be outlined.

Step 1. After the adequate induction of general anesthesia the patient is placed supine on the radiolucent Jackson table. The patient is prepped and draped. A General abdominal surgeon creates an infraumbilical incision, and then using a retroperitoneal or transperitoneal approach as described in detail elsewhere, the L4/5 or L5/S1 disc spaces are identified using fluoroscopic or x-ray guidance.

Step 2. The microscope is now brought in and a complete discectomy is performed which can be verified under direct microscopic vision.

Step 3. The prosthetic disc, embodiment I, II, III, IV, V, VI or VII is placed with forceps directly into the disc space with the horizontal axis of the device aligned with the horizontal axis of the vertebral body. The convex lower aspect of the device is placed above the ventral surface of the thecal sac. The dorsal upper aspect of the prosthesis with its ratcheting screws is in the surgeon's field.

Step 4. The prosthesis is secured with a forceps, and using fluoroscopic guidance, the prosthesis height is expanded to custom fit the vertebral endplate by ratcheting screw 1 with the appropriately designed screwdriver.

Steps 5 and 6 are now identical to steps 5 and 6 used for posterior lumbar placement (Approach A).

The surgical steps necessary to practice the present invention for posterior implantation of the lumbar/thoracic artificial disc, embodiment I, II, III, IV VI or VII into the thoracic disc interspace will now be described.

Step 1. After the adequate induction of general anesthesia the patient is positioned prone on a radiolucent Jackson table. The patient is prepped and draped. Then utilizing fluoroscopic or x-ray guidance, the correct and relevant spinous processes and posterior elements are identified. Then using a standard extracorporeal, transpedicular approach, the rib head is removed and the pedicle drilled overlying the appropriate disc space as fully described in detail elsewhere.

Step 2. The microscope is now brought in for appropriate magnification. The discectomy is performed routinely. An endoscope can be employed to verify complete circumferential discectomy.

Step 3. The lumbar/thoracic prosthesis, embodiment I, II, III, IV, V, VI or VIIis introduced into the disc space using a forceps aligning the horizontal axis of the device with the horizontal axis of the vertebral body. The concave surface of the prosthesis is now placed several millimeters under the spinal cord. Specifically designed right-angled screwdrivers, are introduced ventral to the cord, and custom fit the prosthesis to the vertebral endplate by ratcheting the length, height and width of the prosthesis.

Steps 4–6 are now identical to steps 4–6 of the posterior lumbar surgical approach A.

The surgical steps necessary to practice the present invention for the anterior implantation of artificial discs, embodiment I, II, III, IV, V or VI into the thoracic spine will now be described.

Step 1. After the adequate induction of general anesthesia, the patient is positioned on a beanbag in the lateral position, with the right or left side up depending on the side of the disc herniation. A thoracic surgeon now performs a thoracotomy, the lung is deflated, and using fluoroscopic or x-ray guidance, the appropriate disc space is identified and visualized as described in detail elsewhere.

Step 2. The microscope is now brought in and a discectomy is performed routinely. Complete and adequate discectomy is confirmed under direct visualization.

Step 3. The lumbar/thoracic prosthesis, embodiment I, II, III, IV, V, VI or VII is placed with forceps directly into the disc space aligning the horizontal axis of the device with the horizontal axis of the vertebral body. The convex lower surface of the device is placed under the ventral surface of the cord. The concave dorsal surface is facing the surgeon such that there is direct visualization of the ratchetable screws.

Steps 4–6 are now identical to steps 4–6 of the posterior lumbar placement approach A.

FIGS. 13A(1)–13D(3) illustrate an alternative cervical disc embodiment or prosthetic disc 400 which includes a core similar to embodiments I, II, III, IV and V, and it is specifically configured for anterior implantation. These figures illustrate the axial views of this cervical disc alternative embodiment. They illustrate expansion of prosthetic cervical disc height and length. For the cross-sectional axial views of all outer and inner surfaces of the multiple shells, and for the mechanical infrastructure (CSGS), and for the dorsal surgeons view illustrating prosthetic width expansion refer to the corresponding figures illustrating these views for lumbar/thoracic disc alternative embodiments, embodiments I, II, III, IV and V (FIGS. 3, 4, 5B, 7A, and 8). These views are virtually identical. Because the cervical spine is less rectangular than the lumbar or thoracic spine, and placement is via an anterior approach, the prosthetic implant 400 takes on a more square/rectangular design (FIGS. 13A(1)–13D(3)) as opposed to a boomerang bean-shaped design. The two-dimensional expansile variant for cervical embodiments I–V, i.e. embodiments VI and VII are identical to that illustrated for the Thoracic-Lumbar prosthesis, except for the rectangular design of the cervical titanium shells.

The surgical steps necessary to practice the present invention for anterior implantation of prosthetic discs, embodiment I, II, III, IV, V, VI or VII into the cervical spine will now be described.

Step 1. After the adequate induction of general anesthesia, the patient is positioned supine on the radiolucent Jackson table. An interscapular roll is placed and the patient's neck is prepped and draped. A horizontal incision is made overlying the appropriate disc interspace with the aide of fluoroscopy or x-ray. The platysma is divided, the esophagus and trachea retracted, the anterior spine exposed, and the appropriate disc space verified radiographically as described in detail elsewhere.

Step 2. The microscope is brought in for appropriate magnification of the operative site. A complete discectomy is performed under direct visualization.

Step 3. The cervical prosthesis embodiment, embodiment I, II, III, IV, V or VI is placed with a forceps directly into the disc space aligning the horizontal axis of the device with the horizontal axis of the vertebral body. The dorsal surface of the prosthesis with ratchetable screws is facing the surgeon. The ventral surface of the prosthesis is above the cervical spinal cord.

Step 4. Once the prosthesis is in the disc space above the spinal cord, using fluoroscopic guidance screw 1 is rotated thereby ratcheting the outer titanium shells until they conform to the individual vertebral plate height.

Steps 5 and 6 are now identical to steps 5 and 6 of posterior placement of lumbar/thoracic artificial discs-approach A.

Because the current embodiment of cervical prosthetic discs lack anterior screw fixation, multi-level disc replacements can now be entertained. Furthermore with respect to all the lumbar, thoracic and cervical prosthetic disc embodiments surgically implanted via posterior or anterior approaches, it is unnecessary to have multiple sizes of each prosthesis. For embodiments I–V one lumbar/thoracic prosthesis of each of the five design embodiments can be custom fit for the individual lumbar or thoracic disc space. One cervical prosthesis of each particular design embodiment can be custom fit for the individual cervical disc space. For embodiments VI and VII only two or maximum three length options can be chosen. The ease of placement diminishes operating room time and decreases morbidity and mortality. This feature of Embodiments I II III IV, V, VI and VII is unique compared to all other designs to date.

The present invention may provide an effective and safe technique that overcomes the problems associated with current techniques, and for most degenerative disc conditions it could replace pedicle screw instrumentation and fusions.

What is claimed is:

1. A total artificial expansible disc for placement between two adjacent vertebral end plates, comprising:
at least two pairs of substantially parallel shells, each pair is adapted to interface directly with only one of two adjacent vertebral endplates, each shell moves along at least two same substantially perpendicular axes increasing the space between each shell apart in order to fill a space between adjacent vertebral endplates;
an expansion device having at least one jack mechanism coupled to the shells to actively move the shells apart along the at least two substantially perpendicular axes; and
a core from the group consisting of at least a pair of directly cooperating elements having at least one element that includes a curved shape, a ball, an elastic element and a sheath filled with elastic material, said core being disposed between the pairs of shells and adapted to actively permit the vertebral endplates to move relative to one another.

2. A total artificial expansible disc according to claim 1 wherein the shells include a plurality of spikes that are embedded in the vertebral endplates.

3. A total artificial expansible disc according to claim 1 wherein the core is fabricated from an elastic material.

4. A total artificial expansible disc according to claim 1 wherein the core is fabricated from a material selected from a group of materials comprising rubber, silicone, or polyurethane.

5. A total artificial expansible disc according to claim 1 wherein the core includes an expandable elastomeric sheath that is molded to the inner surfaces of the shells and that can expand to substantially fill the space between the shells.

6. A total artificial expansible disc according to claim 5 wherein a curable liquefied material is injected into the sheath causing it to expand.

7. A total artificial expansible disc according to claim 6 wherein the liquefied material is selected from a group of materials comprising
polycarbonateurethane, polyurethane, polyvinyl alcohol, or protein hydrogel.

8. A total artificial expansible disc according to claim 6 wherein the sheath includes a coil and a port.

9. A total artificial expansible disc according to claim 1 that further includes at least two inner shells disposed near the moveable shells, the first inner shell disposed near the outer moveable shells which form a rostral leaflet, and the second inner shell disposed near the outer moveable shells which form a caudal leaflet; the first inner shell having a trough and the second inner shell having a protruding ball that cooperates with the trough.

10. A total artificial expansible disc according to claim 9 that further includes intermediate plates disposed between the outer and inner shells.

11. A total artificial expansible disc according to claim 10 wherein the outer shells and the inner plates are made from titanium and the inner shells are made from stainless steel.

12. A total artificial expansible disc according to claim 1 that further includes at least two inner shells disposed near the moveable shells, the first inner shell disposed near the outer moveable shells which form a rostral leaflet, and the second inner shell disposed near the outer moveable shells which form a caudal leaflet; the first inner shell having a convex shape and the second inner shell having a convex shape.

13. A total artificial expansible disc according to claim 12 that further includes intermediate plates disposed between the outer and inner shells.

14. A total artificial expansible disc according to claim 10 wherein the outer shells and the inner plates are made from titanium and the inner shells are made from UHMWPE.

15. A total artificial expansible disc according to claim 1 that further includes at least two inner shells disposed near the moveable shells, the first inner shell disposed near the outer moveable shells which form a rostral leaflet, and the second inner shell disposed near the outer moveable shells which form a caudal leaflet; the first inner shell having a substantially planar shape and the second inner shell having a convex shape.

16. A total artificial expansible disc according to claim 15 that further includes an intermediate plate disposed between the outer and inner shells of the caudal leaflet.

17. A total artificial expansible disc according to claim 10 wherein the outer shells, the first inner shell and the intermediate plate are made from titanium, and the second inner convex shell is made from UHMWPE.

18. A total artificial expansible disc according to claim 1 wherein the moveable shells form a dorsal pair having rostral and caudal shells, and the moveable shells form a ventral pair having rostral and caudal shells; and wherein the dorsal pair and ventral pair move apart.

19. A total artificial expansible disc according to claim 18 wherein the moveable shells form a rostral pair having dorsal and ventral shells, and the moveable shells form a caudal pair having dorsal and ventral shells; and wherein the rostral pair and caudal pair move apart.

20. A total artificial expansible disc according to claim 1 wherein the jack mechanism includes a plurality of arms, and the jack mechanism includes a jackscrew that is activated by a screw disposed at apices formed by jackscrew arms.

21. A total artificial expansible disc according to claim 20 wherein the jackscrew mechanism includes a plurality of arms, and the jackscrew mechanism is activated by either at least one contraction wire disposed at apices of the jackscrew arms or a screw disposed at apices of the of the jackscrew arms.

22. A total artificial expansible disc according to claim 1 wherein the jack mechanism includes a plurality of arms, and the jack mechanism is activated by at least one contraction wire disposed at apices of arms.

23. A total artificial expansible disc according to claim 22 wherein the contraction wire is responsive to a power supply disposed externally of the jack mechanism.

24. A total artificial expansible disc according to claim 22 wherein the contraction wire is responsive to a power supply disposed internally of the jack mechanism.

25. A total artificial expansible disc according to claim 22 wherein jackscrew included two contraction wires one being disposed in a substantially vertical direction and the other being disposed in substantially a horizontal direction.

26. A total artificial expansible disc according to claim 1 wherein the moveable shells form a boomerang shape.

27. A total artificial expansible disc for placement between two adjacent vertebral endplates, comprising:
at least two pairs of substantially parallel shells, each pair is adapted to interface directly with only one of two adjacent vertebral endplates, each shell moves along at least two same substantially perpendicular axes increasing the space between each shell apart in order to fill a space between adjacent vertebral endplates;
at least one expansion mechanism coupled to the shells to actively move the shells apart along the at least two substantially perpendicular axes; and
a core from the group consisting of at least a pair of directly cooperating elements having at least one element that includes a curved shape, a ball, an elastic element and a sheath filled with elastic material, said core being disposed between the pairs of shells and adapted to actively permit the vertebral endplates to move relative to one another.

28. A total artificial expansible disc according to claim 27 wherein the shells include a plurality of spikes that are adapted to be embedded in the vertebral endplates.

29. A total artificial expansible disc according to claim 27 wherein the core is fabricated from an elastic material.

30. A total artificial expansible disc according to claim 27 wherein the core is fabricated from a material selected from a group of materials comprising rubber, silicone, or polyurethane.

31. A total artificial expansible disc according to claim 27 wherein the core includes an expandable elastomeric sheath that is molded to the inner surfaces of the shells and that can expand to substantially fill the space between the shells.

32. A total artificial expansible disc according to claim 31 wherein a curable liquefied material is injected into the sheath causing it to expand.

33. A total artificial expansible disc according to claim 32 wherein the liquefied material is selected from a group of materials comprising polycarbonate, polyurethane, polyvinyl alcohol, or protein hydrogel.

34. A total artificial expansible disc according to claim 32 wherein the sheath includes a coil and a port.

35. A total artificial expansible disc according to claim 27 that further includes at least two inner shells disposed near the moveable shells, the first inner shell disposed near the outer moveable shells which form a rostral leaflet, and the second inner shell disposed near the outer moveable shells which form a caudal leaflet; the first inner shell having a trough and the second inner shell having a protruding ball that cooperates with the trough.

36. A total artificial expansible disc according to claim 35 that further includes intermediate plates disposed between the outer and inner shells.

37. A total artificial expansible disc according to claim 36 wherein the outer shells and the inner plates are made from titanium and the inner shells are made from stainless steel.

38. A total artificial expansible disc according to claim 27 that further includes at least two inner shells disposed near the moveable shells, the first inner shell disposed near the outer moveable shells which form a rostral leaflet, and the second inner shell disposed near the outer moveable shells which form a caudal leaflet; the first inner shell having a convex shape and the second inner shell having a convex shape.

39. A total artificial expansible disc according to claim 38 that further includes intermediate plates disposed between the outer and inner shells.

40. A total artificial expansible disc according to claim 36 wherein the outer shells and the inner plates are made from titanium and the inner shells are made from UHMWPE.

41. A total artificial expansible disc according to claim 27 that further includes at least two inner shells disposed near the moveable shells, the first inner shell disposed near the outer moveable shells which form a rostral leaflet, and the second inner shell disposed near the outer moveable shells which form a caudal leaflet; the first inner shell having a substantially planar shape and the second inner shell having a convex shape.

42. A total artificial expansible disc according to claim 41 that further includes an intermediate plate disposed between the outer and inner shells of the caudal leaflet.

43. A total artificial expansible disc according to claim 36 wherein the outer shells, the first inner shell and the intermediate plate are made from titanium, and the second inner convex shell is made from UHMWPE.

44. A total artificial expansible disc according to claim 27 wherein the moveable shells form a dorsal pair having rostral and caudal shells, and the moveable shells form a ventral pair having rostral and caudal shells; and wherein the dorsal pair and ventral pair move apart.

45. A total artificial expansible disc according to claim 44 wherein the moveable shells form a rostral pair having dorsal and ventral shells, and the moveable shells form a caudal pair having dorsal and ventral shells; and wherein the rostral pair and caudal pair move apart.

46. A total artificial expansible disc according to claim 45 that further includes at least one removable expansion bar moving the dorsal and ventral shells apart.

47. A total artificial expansible disc according to claim 46 that further includes at least one removable expansion bar for moving the rostral and caudal shells apart.

48. A total artificial expansible disc according to claim 47 wherein the removable expansion bars include a ratcheting mechanism.

49. A total artificial expansible disc according to claim 47 wherein the core is fabricated from an elastic material.

50. A total artificial expansible disc according to claim 27;
wherein the moveable shells form a left dorsal pair having rostral and caudal shells and a right dorsal pair having rostral and caudal shells;
wherein the moveable shells form a left ventral pair having rostral and caudal shells and a right ventral pair having rostral and caudal shells; and
wherein the left and right dorsal pairs simultaneously move apart form the left and right ventral pairs.

51. A total artificial expansible disc according to claim 46;
wherein the left dorsal pair and left ventral pair simultaneously move apart from the right dorsal pair and the right ventral pair.

52. A total artificial expansible disc according to claim 47;
wherein all the rostral shells simultaneously move apart from the caudal shells.

53. A total artificial expansible disc according to claim 27 wherein the moveable shells form a boomerang shape.

54. A total artificial expansible disc according to claim 50 wherein the expansion device controls the movement of the moveable shells with three screws disposed on a dorsal shell.

55. A total artificial expansible disc according to claim 27 wherein the expansion device includes a plurality of components that move in response to a rotational control member.

56. A total artificial expansible disc according to claim 55 wherein the expansion device includes a plurality of flexible joints that are adapted to permit relative movement of the shells after being embedded in the vertebral endplates.

57. A method of inserting a total artificial expansible disc between two adjacent vertebral endplates, comprising the steps of:
inserting into an intervertebral disc space defined by two adjacent vertebral endplates, at least two pairs of substantially parallel shells, each shell can move along at least two same substantially perpendicular axes;
expanding all of the shells apart along the at least two substantially perpendicular axes until the shells fill a portion of the disc space with each pair of shells directly contacting only one vertebral body;
providing a core from the group consisting of at least a pair of directly cooperating elements having at least one element that includes a curved shape, a ball, an elastic element and a sheath filled with elastic material;
disposing the core between the pairs of shells permitting the vertebral endplates to move relative to one another.

58. A method according to claim 57 which further includes the step of expanding the pairs of shells along an axis substantially defined by the dorsal and ventral portions of the body.

59. A method according to claim 58 which further includes the step of expanding the pairs of shells along an axis substantially defined by the rostral and caudal portions of the body.

60. A method according to claim 59 which further includes the step of expanding the pairs of shells along an axis substantially defined by the left and right portions of the body.

61. A method according to claim 57 wherein the inserting step is performed from the posterior portion of the body.

62. A method according to claim 61 wherein the inserting step is performed in the lumbar portion of the spine.

63. A method according to claim 61 wherein the inserting step is performed in the thoracic portion of the spine.

64. A method according to claim 61 wherein the inserting step is performed in the cervical portion of the spine.

65. A total artificial expansible disc for placement between two adjacent vertebral endplates, comprising:
 at least two pairs of substantially parallel shells, each pair is adapted to interface directly with only one of two adjacent vertebral endplates, each shell moves along at least two same substantially perpendicular axes increasing the space between each shell apart in order to fill a space between adjacent vertebral endplates;
 at least one expansion mechanism coupled to the shells to actively move the shells apart along the at least two substantially perpendicular axes; and
 a core of elastomeric material disposed between the pairs of shells and positioned in the center of the vertebral endplates after the shells have been moved apart to the outer periphery of the vertebral endplates, and adapted to actively permit the vertebral endplates to move relative to one another.

66. A method of inserting a total artificial expansible disc between two adjacent vertebral endplates, comprising the steps of:
 inserting into an intervertebral disc space defined by two adjacent vertebral endplates, at least two pairs of substantially parallel shells, each shell can move along at least two same substantially perpendicular axes;
 expanding all of the shells apart along the at least two substantially perpendicular axes until the shells fill a portion of the disc space with each pair of shells directly contacting only one vertebral body;
 providing a core of elastomeric material that is positioned in the center of the vertebral endplates after the shells have been moved apart to the outer periphery of the vertebral endplates, and;
 disposing the core between the pairs of shells permitting the vertebral endplates to move relative to one another.

67. A total artificial expansible disc for posterior placement between two adjacent vertebral endplates, comprising:
 at least two pairs of substantially parallel shells, each pair is adapted to interface directly with only one of two adjacent vertebral endplates, each shell moves along at least two same substantially perpendicular axes increasing the space between each shell apart in order to fill a space between adjacent vertebral endplates;
 at least one expansion mechanism coupled to the shells to actively move the shells apart along the at least two substantially perpendicular axes; and
 a core, including a ball and a trough, disposed between the pairs of shells and positioned in the center of the vertebral endplates after the shells have been moved apart to the outer periphery of the vertebral endplates, and adapted to actively permit the vertebral endplates to move relative to one another.

68. A method of posteriorly inserting a total artificial expansible disc between two adjacent vertebral endplates, comprising the steps of:
 inserting into an intervertebral disc space defined by two adjacent vertebral endplates, at least two pairs of substantially parallel shells, each shell can move along at least two same substantially perpendicular axes;
 expanding all of the shells apart along the at least two substantially perpendicular axes until the shells fill a portion of the disc space with each pair of shells directly contacting only one vertebral body;
 providing a core, including a ball and a trough, that is positioned in the center of the vertebral endplates after the shells have been moved apart to the outer periphery of the vertebral endplates, and;
 disposing the core between the pairs of shells permitting the vertebral endplates to move relative to one another.

* * * * *